US007625873B2

(12) United States Patent
Geller et al.

(10) Patent No.: US 7,625,873 B2
(45) Date of Patent: *Dec. 1, 2009

(54) ANTISENSE ANTIBACTERIAL METHOD AND COMPOUND

(75) Inventors: Bruce L. Geller, Corvallis, OR (US); Jesse D. Deere, Davis, CA (US); Patrick L. Iversen, Corvallis, OR (US); Dwight D. Weller, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 106 days.

This patent is subject to a terminal disclaimer.

(21) Appl. No.: 11/432,216

(22) Filed: May 10, 2006

(65) Prior Publication Data
US 2007/0049542 A1 Mar. 1, 2007

Related U.S. Application Data

(63) Continuation-in-part of application No. 11/173,847, filed on Jul. 1, 2005.

(60) Provisional application No. 60/585,112, filed on Jul. 2, 2004.

(51) Int. Cl.
*A01N 43/04* (2006.01)
*C12Q 1/68* (2006.01)
*C12N 15/74* (2006.01)
*C07H 21/02* (2006.01)
*C07H 21/04* (2006.01)

(52) U.S. Cl. ............................ 514/44; 435/6; 435/91.1; 435/91.31; 435/471; 536/23.1; 536/24.32; 536/24.5

(58) Field of Classification Search .................... 435/6, 435/91.1, 91.31, 471; 514/44; 536/23.1, 536/24.32, 24.5
See application file for complete search history.

(56) References Cited

U.S. PATENT DOCUMENTS

| 5,185,444 | A | 2/1993 | Summerton |
| 5,749,847 | A | 5/1998 | Zewert et al. |
| 5,892,023 | A | 4/1999 | Pirotzky et al. |
| 6,030,954 | A * | 2/2000 | Wu et al. ...................... 514/44 |
| 6,060,456 | A | 5/2000 | Arnold et al. |
| 6,133,246 | A * | 10/2000 | McKay et al. ................ 514/44 |
| 6,228,579 | B1 | 5/2001 | Zyskind et al. |
| 6,239,265 | B1 | 5/2001 | Cook |
| 6,495,663 | B1 | 12/2002 | Rothbard et al. |
| 6,677,153 | B2 | 1/2004 | Iversen |
| 6,784,291 | B2 | 8/2004 | Iversen et al. |
| 6,828,105 | B2 | 12/2004 | Stein et al. |
| 6,841,542 | B2 | 1/2005 | Bartelmez |
| 7,049,431 | B2 | 5/2006 | Iversen et al. |
| 7,094,765 | B1 | 8/2006 | Iversen et al. |
| 2003/0095953 | A1 | 5/2003 | Cabot et al. |
| 2003/0166588 | A1 | 9/2003 | Iversen et al. |
| 2003/0175767 | A1 | 9/2003 | Davis et al. |
| 2003/0224353 | A1 | 12/2003 | Stein et al. |
| 2006/0281701 | A1 | 12/2006 | Stein et al. |
| 2007/0021362 | A1 | 1/2007 | Geller et al. |
| 2007/0135333 | A1 | 6/2007 | Geller et al. |
| 2008/0194463 | A1 | 8/2008 | Weller et al. |

FOREIGN PATENT DOCUMENTS

| WO | WO 01/49775 A2 | 7/2001 |
| WO | WO 02/079467 | * 10/2002 |
| WO | WO 02/079467 A2 | 10/2002 |
| WO | WO 02/094250 | * 11/2002 |
| WO | WO 2006/047683 A1 | 5/2006 |

OTHER PUBLICATIONS

International Search Report for PCT/US05/023553, AVI Biopharma, Inc., Nov. 8, 2006.
Deere et al., *Antimicrobial Agents and Chemotherapy*, 49(1):249-255 (2005).
Dryselius et al., *Oligonucleotides*, 13(6):427-33 (2003).
Geller et al., *Antimicrob Agents Chemother.*, 47(10):3233-9 (2003).
Good et al., *Nature Biotechnology*, 19(4):360-364 (2001).
Nielsen, P. E., *Expert Opinion on Investigational Drugs*, 10(2):331-341 (2001).
Wang et al., *FEMS Microbiology Letters*, 220(2):171-176 (2003).
Agrawal, Sudhir, *Tibtech*, 14:376-387 (1996).
Agrawal et al., *Molecular Med. Today*, 6:72-81 (2000).
Bailey, C. P., J. M. Dagle et al., "Cationic oligonucleotides can mediate specific inhibition of gene expression in Xenopus oocytes." *Nucleic Acids Res*, 26(21): 4860-7 (1998).
Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19): 11047-52. (1998).
Branch et al., *Trends in Biochem. Sci.*, 23:45-50 (1998).
Chirilla et al., *Biomaterials*, 23:321-342 (2002).
Crooke, S.T., *Antisense Res. And Applica.*, 1-50. S. Crooke, ed. Springer. (1999).
Gilbert et al., *J. Clinical Epidemiology*, 54:68-85 (2001).
Green et al., *J. Am. Coll. Surg.*, Collective Review 93-105.
Hudziak et al., *Antisnese &Nucleic Acid Drug Dev.*, 6:267-272 (1996).
Jen et al., *Stem Cells*, 18:307-319.

(Continued)

*Primary Examiner*—Jane Zara
(74) *Attorney, Agent, or Firm*—Seed IP Law Group PLLC

(57) ABSTRACT

A method and antisense compound for inhibiting the growth of pathogenic bacterial cells are disclosed. The compound contains no more than 12 nucleotide bases and has a targeting nucleic acid sequence of no fewer than 10 bases in length that is complementary to a target sequence containing or within 10 bases, in a downstream direction, of the translational start codon of a bacterial mRNA that encodes a bacterial protein essential for bacterial replication. The compound binds to a target mRNA with a $T_m$ of between 50° to 60° C. The relatively short antisense compounds are substantially more active than conventional antisense compounds having a targeting base sequence of 15 or more bases.

6 Claims, 17 Drawing Sheets

OTHER PUBLICATIONS

Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11): 1893-1901 (2000).

Micklefield, J., "Backbone modification of nucleic acids: synthesis, structure and therapeutic applications." *Curr Med Chem*, 8(10):1157-79 (2001).

Nelson, M. H., D. A. Stein, et al. (2005). "Arginine-rich peptide conjugation to morpholino oligomers: effects on antisense activity and specificity." *Bioconjug Chem* 16(4): 959-66.

Palu et al., *J. Biotech.*, 68:1-13 (1999).

Summerton et al., *Antisense & Nucleic Acid Drug Development*, 7:63-70 (1997).

Summerton et al., *Biochim et. Biophys. ACTA*, 1489:141-158 (1999).

Summerton, J. and D. Weller (1997). "Morpholino antisense oligomers: design, preparation, and properties." *Antisense Nucleic Acid Drug Dev* 7(3) : 187-95.

Zollinger et al., *Transactions of Royal Soc of Tropical Medicine and Hygiene.*, 85(Supp. 1) pp. 37-43 (1991).

Blommers, M. J., U. Pieles, et al., "An approach to the structure determination of nucleic acid analogues hybridized to RNA. NMR studies of a duplex between 2'-OMe RNA and an oligonucleotide containing a single amide backbone modification." *Nucleic Acids Res.*, 22(20):4187-94 (1994).

Bramhill, D., "Bacterial cell division", *Annu Rev Cell Dev Biol.*, 13:395-424 (1997).

Cross et al., "Solution structure of an RNA x DNA hybrid duplex containing a 3'-thioformacetal linker and an RNA A-tract", *Biochemistry*, 36(14):4096-107 (1997).

Dagle et al., "Targeted elimination of zygotic messages in Xenopus laevis embryos by modified oligonucleotides possessing terminal cationic linkages", *Nucleic Acids Research*, 28(10):2153-2157 (2000).

Donachie, W. D., "The cell cycle of *Escherichia coli*", *Annu Rev Microbiol.*, 47:199-230 (1993).

Gait et al., "Synthetic-analogues of polynucleotides XII. Synthesis of thymidine derivatives containing an oxyacetamido- or an oxyformamido-linkage instead of a phosphodiester group", *J Chem Soc [Perkin 1]*0(14):1684-6 (1974).

Galloway, S. M. and Raetz, C.R., "A mutant of *Escherichia coli* defective in the first step of endotoxin biosynthesis", *J. Biol Chem.*, 265(11):6394-402 (1990).

Geller, B. L. and Green, H.M., Translocation of pro-OmpA across inner membrane vesicles of *Escherichia coli* occurs in two consecutive energetically distinct steps', *J Biol Chem.*, 264(28):16465-9 (1989).

Gerdes et al., "Experimental determination and system level analysis of essential genes in *Escherichia coli* MG1655", *J Bacteriol.*, 185(19):5673-84 (2003).

Good et al., "Antisense PNA effects in *Escherichia coli* are limited by the outer-membrane LPS layer", *Microbiology*, 146( Pt 10):2665-70 (2000).

Hale, C. A. and de Boer, P.A., "Recruitment of ZipA to the septal ring of *Escherichia coli* is dependent on FtsZ and independent of FtsA", *J Bacteriol.*, 181(1):167-76.

Jackowski S. and Rock, C.O., "Ratio of active to inactive forms of acyl carrier protein in *Escherichia coli*", *J Biol Chem.*, 258(24):15186-91 (1983).

Jackson et al., "*Escherichia coli* O157:H7 diarrhoea associated with well water and infected cattle on an Ontario farm", *Epidemiol. Infect.*, 120(1):17-20 (1998).

Knudsen, H. and Nielsen, P.E., "Antisense properties of duplex- and triplex-forming PNAs", *Nucleic Acids Res.*, 24(3):494-500 (1996).

Lesnikowski et al. "Octa(thymidine methanephosphonates) of partially defined stereochemistry: synthesis and effect of chirality at phosphorus on binding to pentadecadeoxyriboadenylic acid", *Nucleic Acids Res.*, 18(8):2109-15 (1990).

Lutkenhaus, J. and Addinall, S.G., "Bacterial cell division and the Z ring", *Annu Rev Biochem.*, 66:93-116 (1997).

Mertes, M. P. and Coats, E.A., "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate", *J Med Chem.*, 12(1):154-7 (1969).

Miyada, C.G. and Wallace, R.B., "Oligonucleotide hybridization techniques", *Methods Enzymol.*, 154:94-107 (1987).

Moulton, H. M. and J. D. Moulton, "Peptide-assisted delivery of steric-blocking antisense oligomers." *Curr Opin Mol Ther.*, 5(2):123-32 (2003).

Moulton et al., "HIV Tat peptide enhances cellular delivery of antisense morpholino oligomers", *Antisense Nucleic Acid Drug Dev.*, 13:31-43 (2003).

Moulton et al., "Cellular uptake of antisense morpholino oligomers conjugated to arginine-rich peptides", *Bioconjugate Chem.*, 15:290-299 (2004).

Nielsen, P. E., "Peptide nucleic acids: on the road to new gene therapeutic drugs", *Pharmacol Toxicol.*, 86(1):3-7 (2000).

Nikaido, H., "Transport across the bacterial outer membrane", *J Bioenerg Biomembr.*, 25(6):581-9, (1993).

O'Ryan et al., *Clinical Virology Manual*, Second Edition, Elviser, New York, Chapter 22, pp. 361-396 (1992),.

Partridge et al., "A simple method for delivering morpholino antisense oligos into the cytoplasm of cells", *Antisense Nucleic Acid Drug Dev.*, 6(3):169-75 (1996).

Petersen et al., "Synthesis of thymidine dimers containing piperazine in the internucleoside linkage and their incorporation into oligodeoxynucleotides", *Tetrahedron*, 51:2145-2154 (1995).

Polacco, M. L. and Cronan, Jr., J.E., "A mutant of *Escherichia coli* conditionally defective in the synthesis of holo-[acyl carrier protein]", *J. Biol Chem.*, 256(11):5750-4 (1981).

Rahman et al., "Antibacterial activity and inhibition of protein synthesis in *Escherichia coli* by antisense DNA analogs", *Antisense Res Dev.*, 1(4):319-27 (1991).

Stein et al., "A specificity comparison of four antisense types: morpholino, 2'-O-methyl RNA, DNA, and phosphorothioate DNA", *Antisense & Nucleic Acid Drug Development*, 7(3):151-7 (1997).

Zhang, Y. and Cronan, Jr., J.E., "Polar allele duplication for transcriptional analysis of consecutive essential genes: application to a cluster of *Escherichia coli* fatty acid biosynthetic genes", *J. Bacteriol.*, 178(12):3614-20 (1996).

Zuker, M., "Mfold web server for nucleic acid folding and hybridization prediction", *Nucleic Acids Res.*, 31(13):3406-15 (2003).

Summerton, J.E., "Morpholinos and PNAs Compared", from "Peptide Nucleic Acids, Morpholinos, and Related Antisense Biomolecules", CG Janson and MJ During, Eds., Kluwer Academic / Plenum Publishers, New York, pp. 89 and 98-101 (2006).

Egholm, M. et al., "PNA Hybridezes to Complementary Oligonucleotdies Obeying the Watson-Crock Hydrogen-Bonding Rules", *Nature*, 365:566-568 (1993).

Agrawal et al., "Oligodeoxynucleoside phosphoramidates and phosphorothioates as inhibitors of human immunodeficiency virus", *Proc. Natl. Acad Sci.*, 85(19):7079-7083 (1988).

Tan, X.X. et al., "Peptide nucleic acid antisense oligomer as a therapeutic strategy against bacterial infection: proof of principle using mouse intraperitoneal infection", *Antimicrobial Agents and Chemotherapy*,49(8):3203-3207 (2005).

Nielsen, P.E. et al., "Sequence-Selective Recognition of DNA by Strand Displacement with a Thymine Substituted Polyamide", *Science*, 254: 1497-1500 (1991).

\* cited by examiner

ANTISENSE ANTIBACTERIAL METHOD AND COMPOUND

This is a continuation-in-part of U.S. patent application Ser. No. 11/173,847, filed Jul. 1, 2005, which claims the benefit of U.S. Provisional Application No. 60/585,112, filed Jul. 2, 2004. Both applications are incorporated in their entirety herein by reference.

FIELD OF THE INVENTION

The present invention relates to oligonucleotide compounds that are antisense to bacterial genes and methods for use of such compounds in inhibiting bacterial growth, e.g., in an infected mammalian subject.

REFERENCES

Blommers, M. J., et al., *Nucleic Acids Res* 22(20):4187-94, (1994).
Bramhill, D., *Annu Rev Cell Dev Biol* 13:395-424.
Cross, C. W., et al., *Biochemistry* 36(14): 4096-107, (1997).
Donachie, W. D., *Annu Rev Microbiol* 47:199-230, (1993).
Dryselius, R., et al., *Oligonucleotides* 13(6):427-33, (2003).
Frimodt-Moller, N., J., et al., *HANDBOOK OF ANIMAL MODELS OF INFECTION.*, San Diego, Calif., Academic Press, (1999).
Gait, M. J., et al., *J Chem Soc [Perkin 1]* 0(14):1684-6, (1974).
Galloway, S. M. and Raetz, C. R., *J Biol Chem* 265(11): 6394-402, (1990).
Geller, B. L., et al., *Antimicrob Agents Chemother* 47(10): 3233-9, (2003).
Geller, B. L. and Green, H. M., *J Biol Chem* 264(28): 16465-9, (1989).
Gerdes, S. Y., et al., *J Bacteriol* 185(19):5673-84, (2003).
Good, L., et al., *Nat Biotechnol* 19(4):360-4, (2001).
Good, L., et al., *Microbiology* 146 (Pt 10):2665-70, (2000).
Hale, C. A. and de Boer, P. A., *J Bacteriol* 181(1):167-76, (1999).
Jackowski, S. and Rock, C. O., *J Biol Chem* 258(24): 15186-91, (1983).
Jackson, et al., *Epidemiol. Infect* 120(1):17-20, (1998).
Knudsen, H. and Nielsen, P. E., *Nucleic Acids Res* 24(3): 494-500, (1996).
Lesnikowski, Z. J., et al., *Nucleic Acids Res* 18(8):2109-15, (1990).
Lutkenhaus, J. and Addinall, S. G., *Annu Rev Biochem* 66:93-116, (1997).
Mertes, M. P. and Coats, E. A., *J Med Chem* 12(1):154-7, (1969).
Miyada, C. G. and Wallace, R. B., *Methods Enzymol.* 154: 94-107, (1987).
Nielsen, P. E., *Pharmacol Toxicol* 86(1):3-7, (2000).
Nikaido, H., *J Bioenerg Biomembr* 25(6):581-9, (1993).
Partridge, M., et al., *Antisense Nucleic Acid Drug Dev* 6(3):169-75, (1996).
Polacco, M. L. and Cronan, Jr., J. E., *J Biol Chem* 256(11): 5750-4, (1981).
Rahman, M. A., et al., *Antisense Res Dev* 1(4):319-27, (1991).
Stein, D., et al., *Antisense Nucleic Acid Drug Dev* 7(3): 151-7, (1997).
Summerton, J., *Biochim Biophys Acta* 1489(1):141-58, (1999).
Summerton, J., et al., *Antisense Nucleic Acid Drug Dev* 7(2):63-70, (1997).
Summerton, J. and Weller, D., *Antisense Nucleic Acid Drug Dev* 7(3):187-95, (1997).
Zhang, Y. and Cronan, Jr., J. E., *J Bacteriol* 178(12):3614-20, (1996).
Zuker, M., *Nucleic Acids Res* 31(13):3406-15, (2003).

BACKGROUND OF THE INVENTION

Currently, there are several types of antibiotic compounds in use against bacterial pathogens, and these compounds act through a variety of anti-bacterial mechanisms. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Some classes of antibiotics act at the level of protein synthesis. Notable among these are the aminoglycosides, such as kanamycin and gentamycin. This class of compounds targets the bacterial 30 S ribosome subunit, preventing the association with the 50 S subunit to form functional ribosomes. Tetracyclines, another important class of antibiotics, also target the 30 S ribosome subunit, acting by preventing alignment of aminoacylated tRNA's with the corresponding mRNA codon. Macrolides and lincosamides, another class of antibiotics, inhibit bacterial synthesis by binding to the 50 S ribosome subunit, and inhibiting peptide elongation or preventing ribosome translocation.

Despite impressive successes in controlling or eliminating bacterial infections by antibiotics, the widespread use of antibiotics both in human medicine and as a feed supplement in poultry and livestock production has led to drug resistance in many pathogenic bacteria. Antibiotic resistance mechanisms can take a variety of forms. One of the major mechanisms of resistance to beta lactams, particularly in Gram-negative bacteria, is the enzyme beta-lactamase, which renders the antibiotic inactive. Likewise, resistance to aminoglycosides often involves an enzyme capable of inactivating the antibiotic, in this case by adding a phosphoryl, adenyl, or acetyl group. Active efflux of antibiotics is another way that many bacteria develop resistance. Genes encoding efflux proteins, such as the tetA, tetG, tetL, and tetK genes for tetracycline efflux, have been identified. A bacterial target may develop resistance by altering the target of the drug. For example, the so-called penicillin binding proteins (PBPs) in many beta-lactam resistant bacteria are altered to inhibit the critical antibiotic binding to the target protein. Resistance to tetracycline may involve, in addition to enhanced efflux, the appearance of cytoplasmic proteins capable of competing with ribosomes for binding to the antibiotic. For those antibiotics that act by inhibiting a bacterial enzyme, such as for sulfonamides, point mutations in the target enzyme may confer resistance.

The appearance of antibiotic resistance in many pathogenic bacteria—in many cases involving multi-drug resistance—has raised the specter of a pre-antibiotic era in which many bacterial pathogens are simply untreatable by medical intervention. There are two main factors that could contribute to this scenario. The first is the rapid spread of resistance and multi-resistance genes across bacterial strains, species, and genera by conjugative elements, the most important of which are self-transmissible plasmids. The second factor is a lack of current research efforts to find new types of antibiotics, due in part to the perceived investment in time and money needed to find new antibiotic agents and bring them through clinical trials, a process that may require a 20-year research effort in some cases.

In addressing the second of these factors, some drug-discovery approaches that may accelerate the search for new antibiotics have been proposed. For example, efforts to screen for and identify new antibiotic compounds by high-throughput screening have been reported, but to date no important lead compounds have been discovered by this route.

Several approaches that involve antisense agents designed to block the expression of bacterial resistance genes or to target cellular RNA targets, such as the rRNA in the 30 S ribosomal subunit, have been proposed (Rahman, Summerton et al. 1991; Good and Nielsen 1998). In general, these approaches have been successful only in a limited number of cases, or have required high antisense concentrations (e.g., (Summerton, Stein et al. 1997), or the requirement that the treated cells show high permeability for antibiotics (Good and Nielsen 1998; Geller, Deere et al. 2003).

There is thus a growing need for new antibiotics that (i) are not subject to the principal types of antibiotic resistance currently hampering antibiotic treatment of bacteria, (ii) can be developed rapidly and with some reasonable degree of predictability as to target-bacteria specificity, (iii) can also be designed for broad-spectrum activity, (iv) are effective at low doses, meaning, in part, that they are efficiently taken up by wild-type bacteria or even bacteria that have reduced permeability for antibiotics, and (v) show few side effects.

SUMMARY OF THE INVENTION

The invention includes, in one general aspect, a method of inhibiting growth of pathogenic bacterial cells, by exposing the cells to a growth-inhibiting amount of a substantially uncharged antisense oligonucleotide compound having (i) no more than 12 nucleotide bases, (II) a targeting nucleic acid sequence of no fewer than 10 bases in length that is complementary to a target sequence containing or within 10 bases, in a downstream direction, of the translational start codon of a bacterial mRNA that encodes a bacterial protein essential for bacterial replication; and (iii) a $T_m$, when hybridized with the target sequence, between 50° to 60° C.

An exemplary oligonucleotide compound for use in the method is composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages, in accordance with the structure:

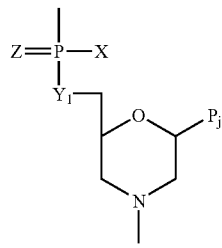

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

The oligonucleotide compound may contain only 10, or only 11 bases, and its nucleic acid sequence may be completely complementary to the mRNA target sequence.

For use in inhibiting a bacterial infection in a mammalian subject, the compound is administered in a therapeutically effective amount, and the treatment may also include treating the subject with another anti-sense or a non-antisense compound having antibacterial activity.

In another aspect, the invention includes an antibacterial compound composed of a substantially uncharged antisense oligonucleotide compound having (i) no more than 12 nucleotide bases, (II) a targeting nucleic acid sequence of no fewer than 10 bases in length that is complementary to a target sequence containing or within 10 bases, in a downstream direction, of the translational start codon of a bacterial mRNA that encodes whose targeting sequence is complementary to a target sequence containing or within 10 bases, in a downstream direction, of the translational start codon of a bacterial mRNA that encodes a bacterial protein selected from the group consisting of acyl carrier protein (acpP), gyrase A subunit (gyrA), and the cell division protein ftsZ; and (iii) a $T_m$, when hybridized with the target sequence, between 50° to 60° C.

Where the compound is directed against a bacterial mRNA that encodes the ftzZ protein, the compound targeting sequence may be complementary to at least ten contiguous bases in a sequence selected from the group consisting of SEQ ID NOS: 1, 4, 7, 10, 13, 16, 17, 19, 22, 25, 28, 31, and 34.

Where the compound is directed against a bacterial mRNA that encodes the acpP protein, the compound targeting sequence may be complementary to at least ten contiguous bases in a sequence selected from the group consisting of SEQ ID NOS: 2, 5, 8, 11, 14, 20, 23, 26, 29, 32, and 35.

Where the compound is directed against a bacterial mRNA that encodes the gyrA protein, the compound targeting sequence may be complementary to at least ten contiguous bases in a sequence selected from the group consisting of SEQ ID NOS: 3, 6, 9, 12, 15, 18, 21, 24, 27, 30, 33, and 36.

The compound may be composed of morpholino subunits and phosphorus-containing intersubunit linkages joining a morpholino nitrogen of one subunit to a 5' exocyclic carbon of an adjacent subunit. The morpholino subunits may be joined by phosphorodiamidate linkages, in accordance with the structure:

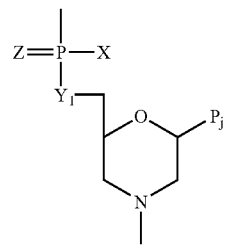

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

The compound may be composed of morpholino subunits linked with the uncharged linkages described above interspersed with linkages that are positively charged at physiological pH. The total number of positively charged linkages is at least 1, preferably at least two and no more than half of the total number of linkages, typically between 2 and 5 positively charged linkages. The positively charged linkages may have the structure above, where X is 1-piperazine.

The compound may contain only 10 or only 11 bases, and its nucleic acid sequence may be completely complementary to the mRNA target sequence.

These and other objects and features of the invention will become more fully apparent when the following detailed description of the invention is read in conjunction with the accompanying drawings.

BRIEF DESCRIPTION OF THE FIGURES

FIG. 2F shows one preferred cationic backbone linkage.

DETAILED DESCRIPTION OF THE INVENTION

I. Definitions

Figure 1A:
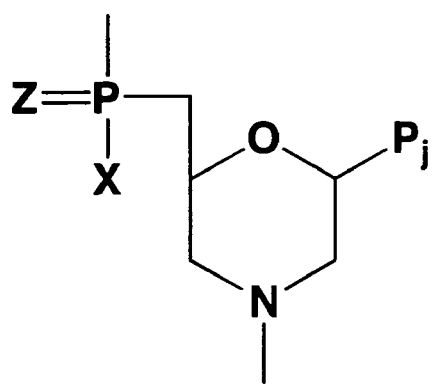
FIGS. 1A-D show several preferred morpholino-type subunits having 5-atom (A), six-atom (B) and seven-atom (C-D) linking groups suitable for forming polymers.
Figure 1B:
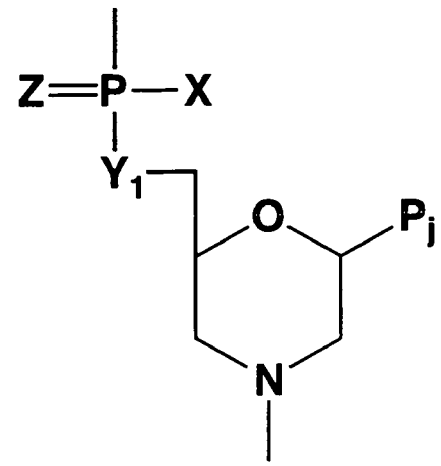
Figure 1C:
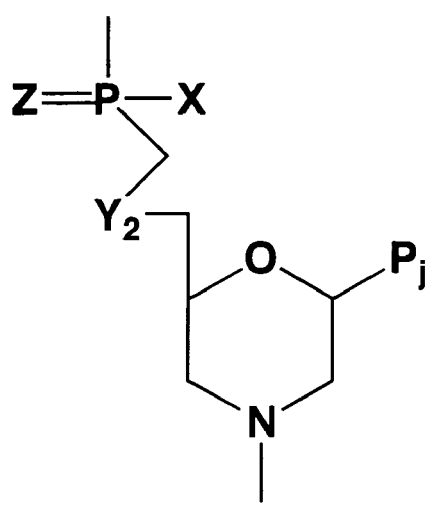
Figure 1D:
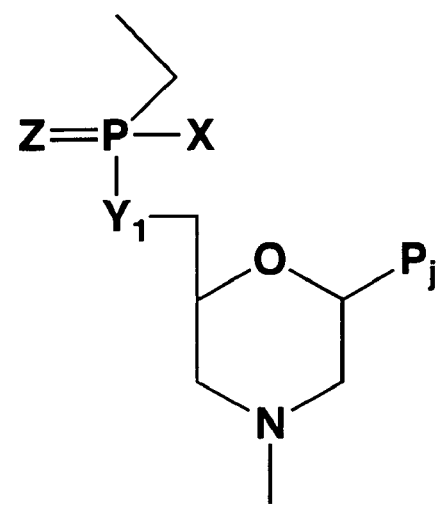

The terms below, as used herein, have the following meanings, unless indicated otherwise:

As used herein, the terms "compound", "agent", "oligomer" and "oligonucleotide" may be used interchangeably with respect to the antisense oligonucleotides or oligonucleotide analogs of the invention.

As used herein, the terms "antisense oligonucleotide" and "antisense oligomer" or "antisense compound" or "antisense oligomer compound" are used interchangeably and refer to a sequence of subunits, each having a base carried on a backbone subunit composed of ribose or other pentose sugar or morpholino group, and where the backbone groups are linked by intersubunit linkages (most or all of which are uncharged) that allow the bases in the compound to hybridize to a target sequence in an RNA by Watson-Crick base pairing, to form an RNA:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes. Exemplary structures for antisense oligonucleotides for use in the invention include the β-morpholino subunit types shown in FIGS. 1A-D. It will be appreciated that a polymer may contain more than one linkage type.

As used herein "antisense oligonucleotide compound," or "antisense compound," or oligonucleotide compound," refers to an "antisense oligonucleotide," or "antisense oligomer," or "oligonucleotide compound," or oligonucleotide analog," that may also include one or more additional moieties conjugated to the oligomer, e.g., at its 3'- or 5'-end, such as a polyethyleneglycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

The terms "oligonucleotide analog" or "oliogonucleotide compound" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, are uncharged at physiological pH, and contain a single phosphorous atom.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide compound" is an oligonucleotide analog composed of morpholino subunit structures of the form shown in FIGS. 1A-1D, where (i) the structures are linked together by phosphorus-containing linkages, one to three atoms long, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. The purine or pyrimidine base-pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Subunit A in FIG. 1 contains a 1-atom phosphorous-containing linkage which forms the five atom repeating-unit backbone shown at A of FIG. 2, where the morpholino rings are linked by a 1-atom phosphonamide linkage. The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom Y1 linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl (C1 to C6) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

Subunits C-D in FIG. 1 are designed for 7-atom unit-length backbones as shown for C and D in FIG. 2. In Structure C of FIG. 1, the X moiety is as in Structure B of FIG. 1 and the moiety Y may be a methylene, sulfur, or preferably oxygen. In Structure D of FIG. 1 the X and Y moieties are as in Structure B of FIG. 1. In all subunits depicted in FIGS. 1A-D, Z is O or S, and $P_i$ or $P_j$ is adenine, cytosine, guanine or uracil.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 2B, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide.

Figure 2A:
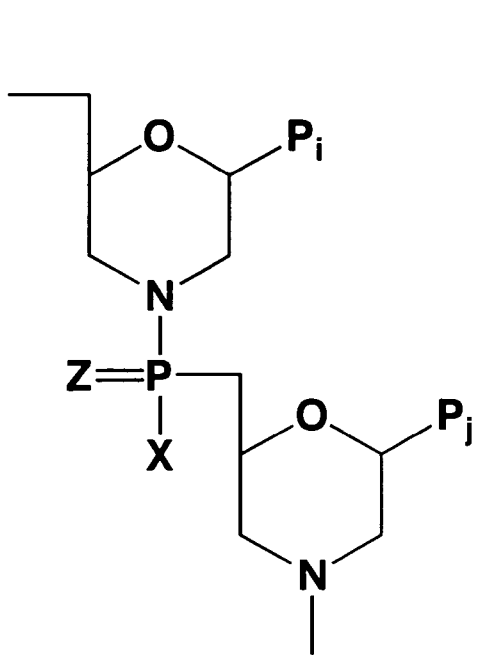
FIGS. 2A-2F show the repeating subunit segment of exemplary morpholino oligonucleotides, where
Figure 2B:
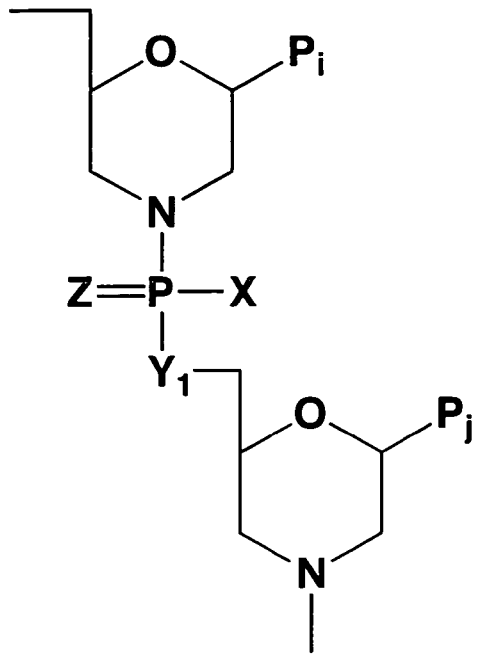

This preferred aspect of the invention is illustrated in FIG. 2B, which shows two such subunits joined by a phosphorodiamidate linkage. Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

As used herein, a "nuclease-resistant" oligomeric molecule (oligomer) is one whose backbone is not susceptible to nuclease cleavage of a phosphodiester bond. Exemplary nuclease resistant antisense oligomers are oligonucleotide analogs, such as phosphorothioate and phosphate-amine DNA (pnDNA), both of which have a charged backbone, and methyl-phosphonate, and morpholino oligonucleotides, all of which may have uncharged backbones.

As used herein, an oligonucleotide or antisense oligomer "specifically hybridizes" to a target polynucleotide if the oligomer hybridizes to the target under physiological conditions, with a Tm greater than 37° C. As will be seen below, the oligomeric compounds of the present invention have Tm values with respect to their target mRNAs of between 50° and 60° C.

The "Tm" of an oligonucleotide compound, with respect to its target mRNA, is the temperature at which 50% of a target sequence hybridizes to a complementary polynucleotide. Tm is determined under standard conditions in physiological saline, as described, for example, in Miyada C. G. and Wallace R. B., 1987.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein the term "analog" with reference to an oligomer means a substance possessing both structural and chemical properties similar to those of a reference oligomer.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, a "base-specific intracellular binding event involving a target RNA" refers to the sequence specific binding of an oligomer to a target RNA sequence inside a cell. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, which is resistant to in vivo degradation by ubiquitous intracellular and extracellular nucleases.

As used herein, "essential bacterial genes" are those genes whose products play an essential role in an organism's functional repertoire as determined using genetic footprinting or other comparable techniques to identify gene essentiality.

An agent is "actively taken up by bacterial cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide compound preferably has a substantially uncharged backbone, as defined below.

As used herein, the terms "modulating expression" and "antisense activity" relative to an oligonucleotide refers to the ability of an antisense oligonucleotide (oligomer) to either enhance or reduce the expression of a given protein by interfering with the expression, or translation of RNA. In the case of reduced protein expression, the antisense oligomer may directly block expression of a given gene, or contribute to the accelerated breakdown of the RNA transcribed from that gene.

As used herein, the term "inhibiting bacterial growth" refers to blocking or inhibiting replication and/or reducing the rate of replication of bacterial cells in a given environment, for example, in an infective mammalian host.

As used herein, the term "pathogenic bacterium," or "pathogenic bacteria," or "pathogenic bacterial cells," refers to bacterial cells capable of infecting a mammalian host and producing infection-related symptoms in the infected host, such as fever or other signs of inflammation, intestinal symptoms, respiratory symptoms, dehydration, and the like.

As used herein, "effective amount" or "therapeutically effective amount" or "growth-inhibiting amount" relative to an antisense oligomer refers to the amount of antisense oligomer administered to a mammalian subject, either as a single dose or as part of a series of doses and which is effective to inhibit bacterial replication in an infected host, by inhibiting translation of a selected bacterial target nucleic acid sequence. The ability to block or inhibit bacterial replication in an infected host may be evidence by a reduction in infection-related symptoms.

As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent.

II. Exemplary oligomer backbones

Examples of nonionic linkages that may be used in oligonucleotide analogs are shown in FIGS. 3A-3F. In these figures, B represents a purine or pyrimidine base-pairing moiety effective to bind, by base-specific hydrogen bonding, to a base in a polynucleotide, preferably selected from adenine, cytosine, guanine, thymidine, uracil and inosine. Suitable backbone structures include carbonate (3A, R=O) and carbamate (3A, R=NH$_2$) linkages (Mertes and Coats 1969; Gait, Jones et al. 1974); alkyl phosphonate and phosphotriester linkages (3B, R=alkyl or —O-alkyl)(Lesnikowski, Jaworska et al. 1990); amide linkages (3C) (Blommers, Pieles et al. 1994); sulfone and sulfonamide linkages (3D, R1, R2=CH$_2$); and a thioformacetyl linkage (3E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 3F.

A preferred oligomer structure employs morpholino-based subunits bearing base-pairing moieties as illustrated in FIGS. 1A-1D, joined by uncharged linkages, as described above. Especially preferred is a substantially uncharged phosphorodiamidate-linked morpholino oligomer, such as illustrated in FIGS. 2A-2D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

A preferred morpholino oligomer is a phosphorodiamidate-linked morpholino oligomer, referred to herein as a PMO. Such oligomers are composed of morpholino subunit structures such as shown in FIG. 2B, where X=NH2, NHR, or NR2 (where R is lower alkyl, preferably methyl), Y=O, and Z=O, and Pi and Pj are purine or pyrimidine base-pairing moieties effective to bind, by base-specific hydrogen bonding, to a base in a polynucleotide, as seen in FIG. 2E. Also preferred are morpholino oligomers where the phosphordiamidate linkages are uncharged linkages as shown in FIG. 2E interspersed with cationic linkages as shown in FIG. 2F where, in FIG. 2B, X=1-piperazino. In another FIG. 2B embodiment, X=lower alkoxy, such as methoxy or ethoxy, Y=NH or NR, where R is lower alkyl, and Z=O.

Important properties of the morpholino-based subunits include: the ability to be linked in a oligomeric form by stable, uncharged backbone linkages; the ability to support a nucleotide base (e.g. adenine, cytosine, guanine, thymidine, uracil and inosine) such that the polymer formed can hybridize with a complementary-base target nucleic acid, including target RNA, Tm values above about 50° C. in relatively short oligomers (e.g., 10-12 bases); the ability of the oligomer to be actively or passively transported into bacterial cells; and the ability of the oligomer:RNA heteroduplex to resist RNAse degradation.

A. Exemplary Oligomeric Compounds

Exemplary backbone structures for antisense oligonucleotides of the invention include the β-morpholino subunit types shown in FIGS. 2A-2D, each linked by an uncharged, phosphorus-containing subunit linkage. FIG. 2A shows a phosphorus-containing linkage which forms the five atom repeating-unit backbone, where the morpholino rings are linked by a 1-atom phosphoamide linkage. FIG. 2B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 2C:
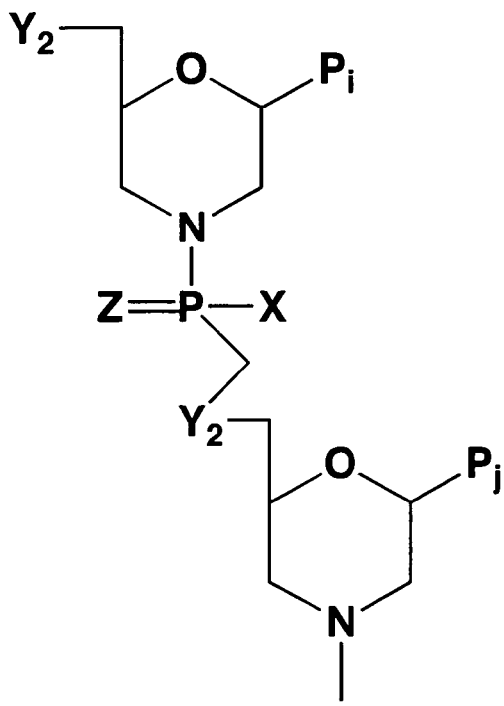
Figure 2D:
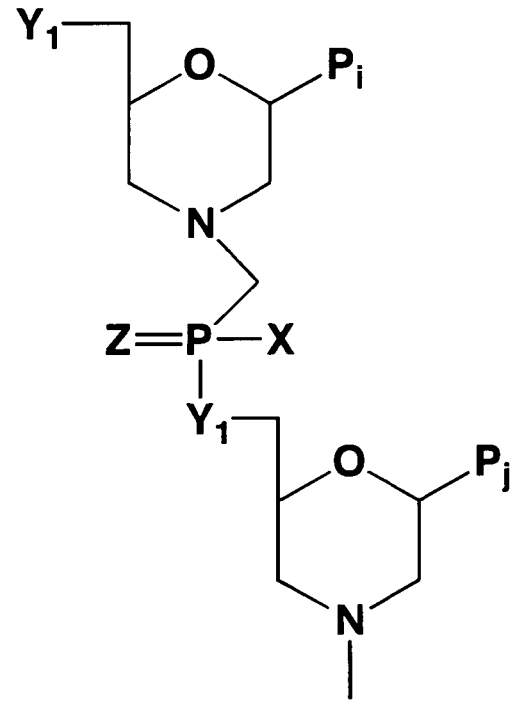
Figure 2E:
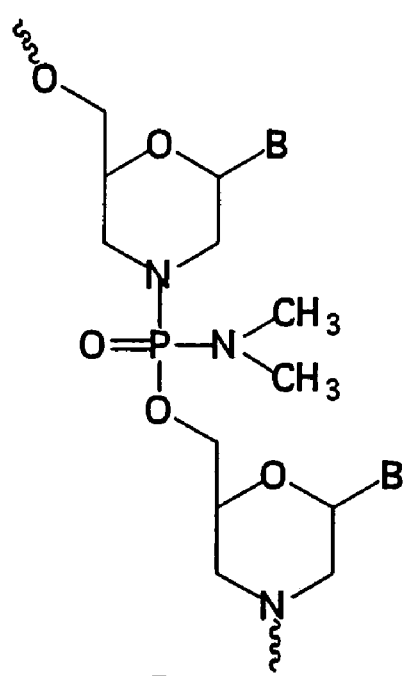
Figure 2F:
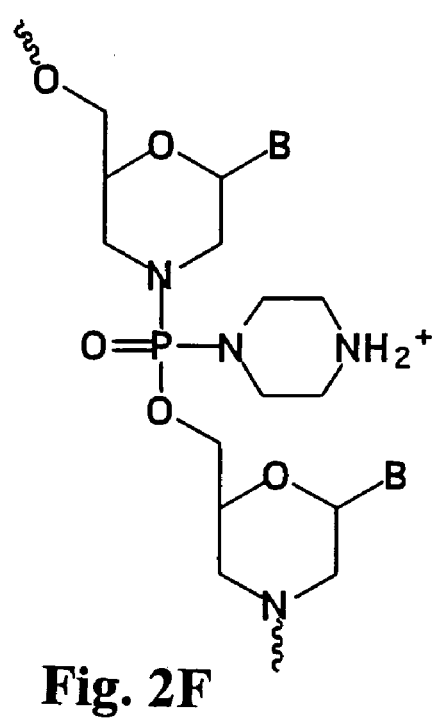
Figure 3A:
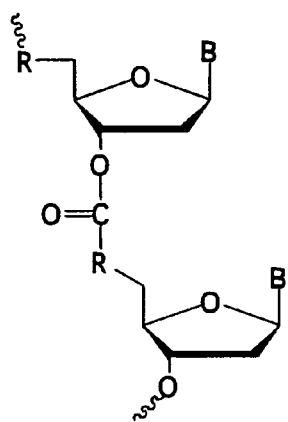
FIGS. 3A-3F show examples of uncharged linkage types in oligonucleotide compounds having ribose subunits.
Figure 3B:
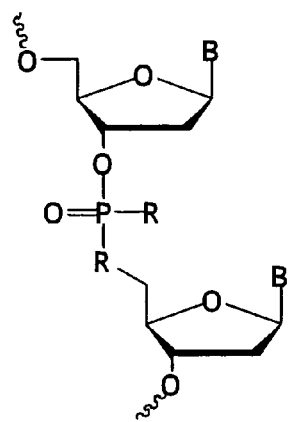
Figure 3C:
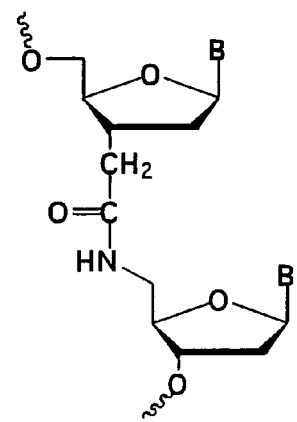
Figure 3D:
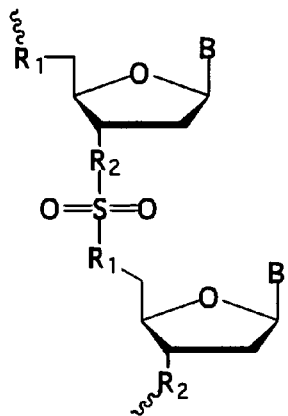
Figure 3E:
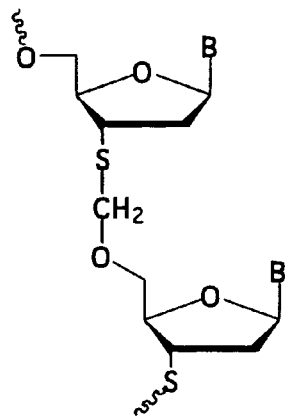
Figure 3F:
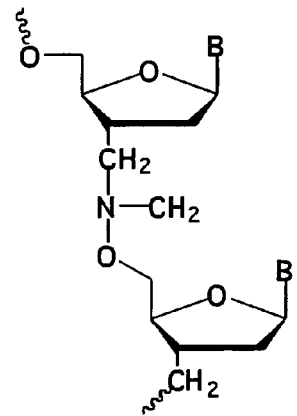

The linkages shown in FIGS. 2C and 2D are designed for 7-atom unit-length backbones. In Structure 2C, the X moiety is as in Structure 2B, and the moiety Y may be methylene, sulfur, or, preferably, oxygen. In Structure 2D, the X and Y moieties are as in Structure 2B. Particularly preferred morpholino oligonucleotides include those composed of morpholino subunit structures of the form shown in FIG. 2B, where X=$NH_2$ or N($CH_3$)$_2$, Y=O, and Z=O.

As noted above, the substantially uncharged oligomer may advantageously include a limited number of charged backbone linkages. One example of a cationic charged phophordiamidate linkage is shown in FIG. 2F. This linkage, in which the dimethylamino group shown in FIG. 2E is replaced by a 1-piperazino group as shown in FIG. 2F, can be substituted for any linkage(s) in the oligomer. By including between one to five such cationic linkages, and more generally, at least one, and preferably at least two, and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

B. Antibacterial Antisense Oligomers

In addition to the structural features described above, the antisense compound of the present invention contains no more than 15 nucleotide bases, preferably no more than 14 nucleotides, more preferably, no more than 12 nucleotide bases, and has a targeting nucleic acid sequence (the sequence which is complementary to the target sequence) of no fewer than 10 contiguous bases. The targeting sequence is complementary to a target sequence containing or within 10 bases, in a downstream direction, of the translational start codon of a bacterial mRNA that encodes a bacterial protein essential for bacterial replication. The compound has a $T_m$, when hybridized with the target sequence, between about 50° to 60° C., although the Tm may be higher, e.g., 65° C. The selection of bacterial targets, and bacterial mRNA target sequences and complementary targeting sequences are considered in the two sections below.

III. Bacterial Targets

This section considers a number of bacterial targets, including pathogenic bacteria, and specific bacterial protein targets against which the antisense compound can be directed.

A. Bacterial Targets

*Escherichia coli* (*E. coli*) is a Gram negative bacteria that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain O157:H7 is estimated to cause 10,000 to 20,000 cases of infection in the United States annually (Federal Centers for Disease Control and Prevention). Hemorrhagic colitis is the name of the acute disease caused by *E. coli* O157:H7. Preschool children and the elderly are at the greatest risk of serious complications. *E. coli* strain O157: H7 was recently reported as the cause the death of four children who ate under cooked hamburgers from a fast-food restaurant in the Pacific Northwest. (See, e.g., Jackson et al., 1998)

Exemplary sequences for enterovirulent *E. coli* strains include GenBank Accession Numbers AB011549, X97542, AF074613, Y11275 and AJ007716.

*Salmonella thyphimurium*, are Gram negative bacteria which cause various conditions that range clinically from localized gastrointestinal infections, gastroenterits (diarrhea, abdominal cramps, and fever) to enteric fevers (including typhoid fever) which are serious systemic illnesses. Salmonella infection also causes substantial losses of livestock.

Typical of Gram-negative bacilli, the cell wall of *Salmonella* spp. contains a complex lipopolysaccharide (LPS) structure that is liberated upon lysis of the cell and may function as an endotoxin, which contributes to the virulence of the organism.

Contaminated food is the major mode of transmission for non-typhoidal salmonella infection, due to the fact that *Salmonella* survive in meats and animal products that are not thoroughly cooked. The most common animal sources are chickens, turkeys, pigs, and cows; in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal Salmonella infection. Non-typhoidal salmonellosis is controlled by hygienic slaughtering practices and thorough cooking and refrigeration of food. Antibiotics are indicated for systemic disease, and Ampicillin has been used with some success. However, in patients under treatment with excessive amounts of antibiotics; patients under treatment with immunsuppressive drugs; following gastric surgery; and in patients with hemolytic anemia, leukemia, lymphoma, or AIDS, Salmonella infection remains a medical problem.

*Pseudomonas* spp. are motile, Gram-negative rods which are clinically important because they are resistant to most antibiotics, and are a major cause of hospital acquired (nosocomial) infections. Infection is most common in: immunocompromised individuals, burn victims, individuals on respirators, individuals with indwelling catheters, IV narcotic users and individual with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Vibrio cholera* is a Gram negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting, however, death can occur from dehydration and loss of essential electrolytes. Antibiotics such as tetracycline have been demonstrated to shorten the course of the illness, and oral vaccines are currently under development.

*Neisseria gonorrhoea* is a Gram negative coccus, which is the causative agent of the common sexually transmitted disease, gonorrhea. *Neisseria gonorrhoea* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram positive coccus which normally colonizes the human nose and is sometimes found on the skin. *Staphylococcus* can cause bloodstream infections, pneumonia, and surgical-site infections in the hospital setting (i.e., nosocomial infections). *Staph. aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently a vancomycin-resistant *Staph. aureus* isolate has also been identified in Japan.

*Mycobacterium tuberculosis* is a Gram positive bacterium which is the causative agent of tuberculosis, a sometimes crippling and deadly disease. Tuberculosis is on the rise and globally and the leading cause of death from a single infectious disease (with a current death rate of three million people per year). It can affect several organs of the human body, including the brain, the kidneys and the bones, however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin), for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram positive coccus and one of the most common causes of bacterial pneumonia as well as middle ear infections (otitis media) and meningitis. Each year in the United States, pneumococcal diseases account for approximately 50,000 cases of bacteremia; 3,000 cases of meningitis; 100,000-135,000 hospitalizations; and 7 million cases of otitis media. Pneumococcal infection causing an estimated 40,000 deaths annually in the United States. Children less than 2 years of age, adults over 65 years of age and persons of any age with underlying medical conditions, including, e.g., congestive heart disease, diabetes, emphysema, liver disease, sickle cell, HIV, and those living in special environments, e.g., nursing homes and long-term care facilities, at highest risk for infection.

Drug-resistant *S. pneumoniae* strains have become common in the United States, with many penicillin-resistant *pneumococci* also resistant to other antimicrobial drugs, such as erythromycin or trimethoprim-sulfamethoxazole.

*Treponema pallidum* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States and it is estimated that 4 million new cases occur each year. The highest rates of infection are in 15 to 19 year olds. Chlamydia is a major cause of non-gonococcal urethritis (NGU), cervicitis, bacterial vaginitis, and pelvic inflammatory disease (PID). Chlamydia infections may have very mild symptoms or no symptoms at all, however, if left untreated Chlamydia infections can lead to serious damage to the reproductive organs, particularly in women. Antibiotics such as azithromycin, erythromycin, ofloxacin, amoxicillin or doxycycline are typically prescribed to treat Chlamydia infection.

*Bartonella henselae.* Cat Scratch Fever (CSF) or cat scratch disease (CSD), is a disease of humans acquired through exposure to cats, caused by a Gram negative rod originally named *Rochalimaea henselae*, and currently known as *Bartonella henselae*. Symptoms include fever and swollen lymph nodes and CSF is generally a relatively benign, self-limiting disease in people, however, infection with *Bartonella henselae* can produce distinct clinical symptoms in immunocompromised people, including, acute febrile illness with bacteremia, bacillary angiomatosis, peliosis hepatis, bacillary splenitis, and other chronic disease manifestations such as AIDS encephalopathy.

The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram negative bacteria; six types of which are known, with most *H. influenza*-related disease caused by type B, or "HIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella dys.*) is a Gram negative rod which causes dysentary. In the colon, the bacteria enter mucosal cells and divide within mucosal cells, resulting in an extensive inflammatory response. Shigella infection can cause severe diarrhea which may lead to dehydration and can be dangerous for the very young, very old or chronically ill. *Shigella dys.* forms a potent toxin (shiga toxin), which is cytotoxic, enterotoxic, neurotoxic and acts as a inhibitor of protein synthesis. Resistance to antibiotics such as ampicillin and TMP-SMX has developed, however, treatment with newer, more expensive antibiotics such as ciprofloxacin, norfloxacin and enoxacin, remains effective.

*Listeria* is a genus of Gram-positive, motile bacteria found in human and animal feces. *Listeria monocytogenes* causes such diseases as listeriosis, meningoencephalitis and meningitis. This organism is one of the leading causes of death from food-borne pathogens especially in pregnant women, newborns, the elderly, and immunocompromised individuals. It is found in environments such as decaying vegetable matter, sewage, water, and soil, and it can survive extremes of both temperatures and salt concentration making it an extremely dangerous food-born pathogen, especially on food that is not reheated. The bacterium can spread from the site of infection in the intestines to the central nervous system and the fetal-placental unit. Meningitis, gastroenteritis, and septicemia can result from infection. In cattle and sheep, listeria infection causes encephalitis and spontaneous abortion.

*Proteus mirabilis* is an enteric, Gram negative commensal, distantly related to *E. coli*. It normally colonizes the human urethra, but is an opportunistic pathogen that is the leading cause of urinary tract infections in catheterized individuals. *P. mirabilis* has two exceptional characteristics: 1) it has very rapid motility, which manifests itself as a swarming phenomenon on culture plates; and 2) it produce urease, which gives it the ability to degrade urea and survive in the genitourinary tract.

*Yersinia pestis* is the causative agent of plague (bubonic and pulmonary) a devastating disease which has killed millions worldwide. The organism can be transmitted from rats to humans through the bite of an infected flea or from human-to-human through the air during widespread infection. *Yersinia pestis* is an extremely pathogenic organism that requires very few numbers in order to cause disease, and is often lethal if left untreated. The organism is enteroinvasive, and can survive and propagate in macrophages prior to spreading systemically throughout the host.

*Bacillus anthracis* is also known as anthrax. Humans become infected when they come into contact with a contaminated animal. Anthrax is not transmitted due to person-to-person contact. The three forms of the disease reflect the sites of infection which include cutaneous (skin), pulmonary (lung), and intestinal. Pulmonary and intestinal infections are often fatal if left untreated. Spores are taken up by macrophages and become internalized into phagolysozomes (membranous compartment) whereupon germination initiates. Bacteria are released into the bloodstream once the infected macrophage lyses whereupon they rapidly multiply, spreading throughout the circulatory and lymphatic systems, a process that results in septic shock, respiratory distress and organ failure. The spores of this pathogen have been used as a terror weapon.

*Burkholderia mallei* is rarely associated with human infection and is more commonly seen in domesticated animals such as horses, donkeys, and mules where it causes glanders, a disease first described by Aristotle. This organism is similar to *B. pseudomallei* and is differentiated by being nonmotile. The pathogen is host-adapted and is not found in the environment outside of its host. Glanders is often fatal if not treated with antibiotics, and transmission can occur through the air, or more commonly when in contact with infected animals. Rapid-onset pneumonia, bacteremia (spread of the organism through the blood), pustules, and death are common outcomes during infection. The virulence mechanisms are not well understood, although a type III secretion system similar to the one from *Salmonella typhimurium* is necessary. No vaccine exists for this potentially dangerous organism which is thought to have potential as a biological terror agent. The genome of this organism carries a large number of insertion sequences as compared to the related *Bukholderia pseudomallei* (below), and a large number of simple sequence repeats that may function in antigenic variation of cell surface proteins.

*Burkholderia pseudomallei* is the organism that causes meliodosis, a disease found in certain parts of Asia, Thailand, and Australia. It is typically a soil organism and has been recovered from rice paddies and moist tropical soil, but as an opportunistic pathogen can cause disease in susceptible individuals such as those that suffer from diabetes mellitus. The organism can exist intracellularly, and causes pneumonia and bacteremia (spread of the bacterium through the bloodstream). The latency period can be extremely long, with infection preceding disease by decades, and treatment can take months of antibiotic use, with relapse a commonly observed phenomenon. Intercellular spread can occur via induction of actin polymerization at one pole of the cell, allowing movement through the cytoplasm and from cell-to-cell. This organism carries a number of small sequence repeats which may promoter antigenic variation, similar to what was found with the *B. mallei* genome.

*Francisella tularensis* was first noticed as the causative agent of a plague-like illness that affected squirrels in Tulare County in California in the early part of the 20th century by Edward Francis. The organism now bears his namesake. The disease is called tularemia and has been noted throughout recorded history. The organism can be transmitted from infected ticks or deerflies to a human, through infected meat, or via aerosol, and thus is a potential bioterrorism agent. It is an aquatic organism, and can be found living inside protozoans, similar to what is observed with Legionella. It has a high infectivity rate, and can invade phagocytic and nonphagocytic cells, multiplying rapidly. Once within a macrophage, the organism can escape the phagosome and live in the cytosol.

Veterinary applications. A healthy microflora in the gastrointestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacteria such as *Salmonella, Campylobacter, Enterococci, Tularemia* and *E. coli*. Bacterial infection in these animals often necessitates therapeutic intervention, which has treatment costs as well being frequently associated with a decrease in productivity.

As a result, livestock are routinely treated with antibiotics to maintain the balance of flora in the gastrointestinal tract. The disadvantages of this approach are the development of antibiotic resistant bacteria and the carry over of such antibiotics and the resistant bacteria into resulting food products for human consumption.

B. Cell Division and Cell Cycle Target Proteins

The antisense oligomers of the invention are designed to hybridize to a region of a bacterial mRNA that encodes an essential bacterial gene. Exemplary genes are those required for cell division, cell cycle proteins, or genes required for lipid biosynthesis or nucleic acid replication. Any essential bacterial gene can be targeted once a gene's essentiality is determined. One approach to determining which genes in an organism are essential is to use genetic footprinting techniques as described (Gerdes, Scholle et al. 2003). In this report, 620 *E. coli* genes were identified as essential and 3,126 genes as dispensable for growth under culture conditions for robust aerobic growth. Evolutionary context analysis demonstrated that a significant number of essential *E. coli* genes are preserved throughout the bacterial kingdom, especially the subset of genes for key cellular processes such as DNA replication and protein synthesis.

In various aspects, the invention provides an antisense oligomer which is a nucleic acid sequence effective to stably and specifically bind to a nucleic acid target sequence which encodes an essential bacterial protein including the following: (1) a sequence specific to a particular strain of a given species of bacteria, such as a strain of *E. coli* associated with food poisoning, e.g., O157:H7 (see Table 1 below); (2) a sequence common to two or more species of bacteria; (3) a sequence common to two related genera of bacteria (i.e., bacterial genera of similar phylogenetic origin); (4) a sequence generally conserved among Gram-negative bacteria; (5) generally conserved among Gram-positive bacteria; or (6) a consensus sequence for essential bacterial protein-encoding nucleic acid sequences in general.

In general, the target for modulation of gene expression using the antisense methods of the present invention comprises an mRNA expressed during active bacterial growth or replication, such as an mRNA sequence transcribed from a gene of the cell division and cell wall synthesis (dcw) gene cluster, including, but not limited to, zipA, sulA, secA, dicA, dicB, dicC, dicF, ftsA, ftsI, ftsN, ftsK, ftsL, ftsQ, ftsW, ftsZ, murC, murD, murE, murF, murG, minC, minD, minE, mraY, mraW, mraZ, seqA and ddlB. See (Bramhill 1997), and (Donachie 1993), both of which are expressly incorporated by reference herein, for general reviews of bacterial cell division and the cell cycle of *E. coli*, respectively. Additional targets include genes involved in lipid biosynthesis (e.g. acpP) and replication (e.g. gyrA).

Cell division in *E. coli* involves coordinated invagination of all 3 layers of the cell envelope (cytoplasmic membrane, rigid peptidoglycan layer and outer membrane). Constriction of the septum severs the cell into 2 compartments and segregates the replicated DNA. At least 9 essential gene products participate in this process: ftsZ, ftsA, ftsQ, ftsL, ftsI, ftsN, ftsK, ftsW and zipA, (Hale and de Boer 1999). Preferred protein targets are the three discussed below.

FtsZ, one of the earliest essential cell division genes in *E. coli*, is a soluble, tubulin-like GTPase that forms a membrane-associated ring at the division site of bacterial cells. The ring is thought to drive cell constriction, and appears to affect cell wall invagination. FtsZ binds directly to a novel integral inner membrane protein in *E. coli* called zipA, an essential component of the septal ring structure that mediates cell division in *E. coli* (Lutkenhaus and Addinall 1997).

GyrA refers to subunit A of the bacterial gyrase enzyme, and the gene therefore. Bacterial gyrase is one of the bacterial DNA topoisomerases that control the level of supercoiling of DNA in cells and is required for DNA replication.

AcpP encodes acyl carrier protein, an essential cofactor in lipid biosynthesis. The fatty acid biosynthetic pathway requires that the heat stable cofactor acyl carrier protein binds intermediates in the pathway.

For each of these latter three proteins, Table 1 provides exemplary bacterial sequences which contain a target sequence for each of a number important pathogenic bacteria. The gene sequences are derived from the GenBank Reference full genome sequence for each bacterial strain (http://www.ncbi.nlm.nih.gov/genomes/lproks.cgi). The gene location on either the positive (+) or negative (−) strand of the genome is listed under "Strand", it being recognized that the strand indicated is the coding sequence for the protein, that is, the sequence corresponding to the mRNA target sequence for that gene. For example, the two *E. coli* genes (ftsZ and acpP) in which the coding sequence is on the positive strand, the sequence is read 5' to 3' in the left-to-right direction. Similarly for the *E. coli* gyrA gene having the coding region on the minus genomic strand, the coding sequence is read as the reverse complement in the right to left direction (5' to 3').

TABLE 1

Exemplary Bacterial Target Gene Sequences

| Organism | GenBank Ref. | Target Gene | Strand | Nucleotide Region |
|---|---|---|---|---|
| *Escherichia coli* | NC 000913 | ftsZ | + | 105305-106456 |
| | | acpP | + | 1150838-1151074 |
| | | gyrA | − | 2334813-2337440 |
| *Escherichia coli* O157:H7 | NC 002655 | ftsZ | + | 109911-111062 |
| | | acpP | + | 1595796-1596032 |
| | | gyrA | − | 3133832-3136459 |
| *Salmonella thyphimurium* | NC 003197 | ftsZ | + | 155683-156834 |
| | | acpP | + | 1280113-1280349 |
| | | gyrA | − | 2373711-2376347 |
| *Pseudomonas aeruginosa* | NC 002516 | ftsZ | − | 4939299-4940483 |
| | | acpP | − | 3324946-3325182 |
| | | gyrA | − | 3556426-3559197 |
| *Vibrio cholera* | NC 002505 | ftsZ | − | 2565047-2566243 |
| | | acpP | + | 254505-254747 |
| | | gyrA | + | 1330207-1332891 |

TABLE 1-continued

Exemplary Bacterial Target Gene Sequences

| Organism | GenBank Ref. | Target Gene | Strand | Nucleotide Region |
|---|---|---|---|---|
| Neisseria gonorrhoea | NC 002946 | ftsZ | − | 1498872-1500050 |
| | | acpP | + | 1724401-1724637 |
| | | gyrA | − | 618439-621189 |
| Staphylococcus aureus | NC 002745 | ftsZ | + | 1165782-1166954 |
| | | gyrA | + | 7005-9674 |
| | | fmhB | − | 2321156-2322421 |
| Mycobacterium tuberculosis | NC 002755 | ftsZ | − | 2407076-2408281 |
| | | acpP | + | 1510182-1510502 |
| | | gyrA | + | 7302-9818 |
| | | pimA | − | 2934009-2935145 |
| | | cysS2 | − | 4014534-4015943 |
| Helicobacter pylori | NC 000915 | ftsZ | + | 1042237-1043394 |
| | | acpP | − | 594037-594273 |
| | | gyrA | + | 752512-754995 |
| Streptococcus pneumoniae | NC 003028 | ftsZ | − | 1565447-1566706 |
| | | acp | + | 396691-396915 |
| | | gyrA | − | 1147387-1149855 |
| Treponema palladium | NC 000919 | ftsZ | + | 414751-416007 |
| | | acp | + | 877632-877868 |
| | | gyrA | + | 4391-6832 |
| Chlamydia trachomatis | NC 000117 | acpP | − | 263702-263935 |
| | | gyrA | − | 755022-756494 |
| Bartonella henselae | NC 005956 | ftsZ | − | 1232094-1233839 |
| | | acpP | + | 623143-623379 |
| | | gyrA | − | 1120562-1123357 |
| Haemophilus influenzae | NC 000907 | ftsZ | + | 1212021-1213286 |
| | | acpP | − | 170930-171160 |
| | | gyrA | − | 1341719-1344361 |
| Listeria monocytogenes | NC 002973 | ftsZ | − | 2102307-2101132 |
| | | acpP | − | 1860771-1860538 |
| | | gyrA | + | 8065-10593 |
| Yersinia pestis | NC 003143 | ftsZ | + | 605874-607025 |
| | | acpP | + | 1824120-1824356 |
| | | gyrA | + | 1370729-1373404 |
| Bacillus anthracis | NC 005945 | ftsZ | − | 3724197-3725357 |
| | | acpP | − | 3666663-3666896 |
| | | gyrA | + | 6596-9067 |
| Burkholderia mallei | NC 006348 | ftsZ | − | 2649616 . . . 2650812 |
| | | acpP | + | 559430 . . . 559669 |
| | | gyrA | − | 459302 . . . 461902 |
| Burkholderia pseudomallei | NC 006350 | ftsZ | − | 3599162-3600358 |
| | | acpP | − | 2944967-2945206 |
| | | gyrA | − | 3036533-3039133 |
| Francisella tularensis | NC 006570 | ftsZ | + | 203748-204893 |
| | | acpP | + | 1421900-1422184 |
| | | gyrA | − | 1637300-1639906 |

C. Selection of Oligomer Target Sequences and Lengths

As noted above, the present invention derives from the discovery herein that oligomeric antisense compounds having a ribose or morpholino subunit backbone are most effective in inhibiting bacterial growth when the subunit length is between 10-12 bases, preferably 11 bases, where the compound contains at least 10 bases, preferably 11-12 bases, that are complementary to the target mRNA sequence. These studies were carried out on bacterial gene expression in pure culture, a bacterial cell-free protein expression system and an in vivo murine peritonitis model, as discussed in detail in the examples below.

Figure 4:
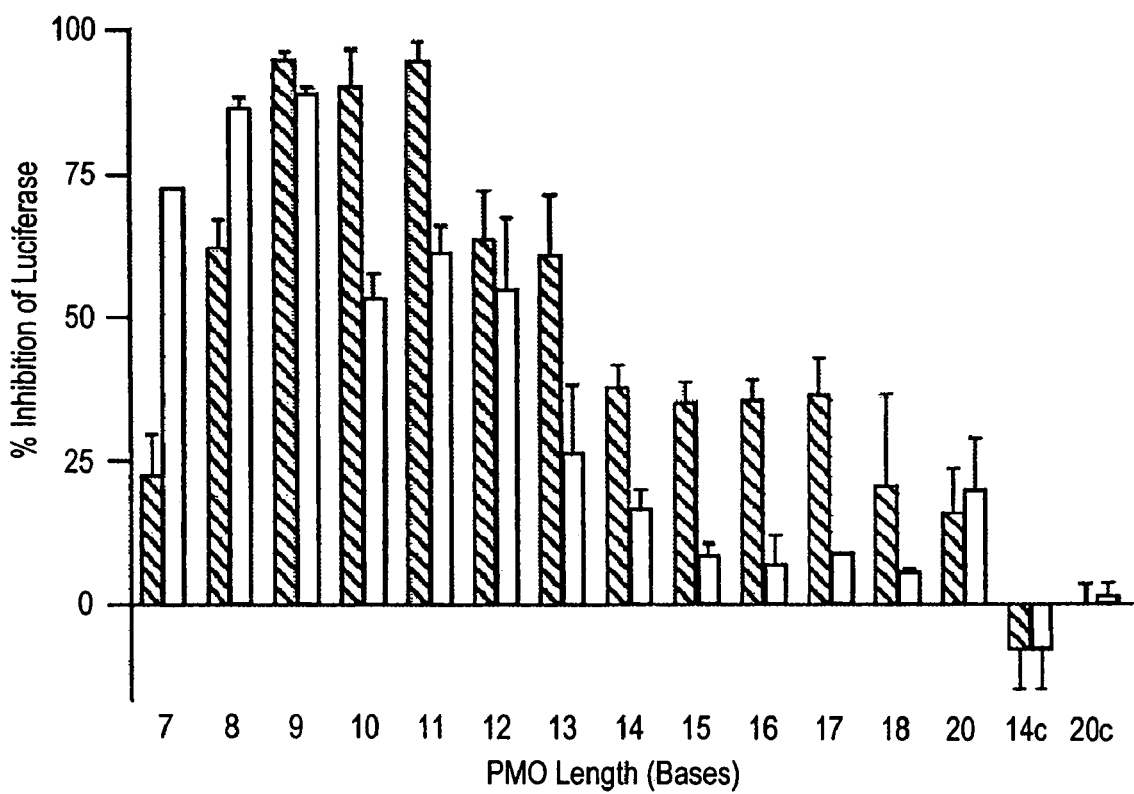
FIG. 4 shows the effect of antisense length on myc-luciferase expression in E. coli SM101. Luciferase activity was measured in cultures of E. coli SM101 (pSE380myc-luc) grown with various lengths of overlapping PMO (20 µM) targeted to the region around the start codon of myc-luc. Striped bars indicate PMO truncated at the 3' end and solid bars are PMO truncated at the 5' end.

Example 1 describes the study on the effect of antisense length and position on inhibition of a marker gene (myc-luc) in E coli, with the results shown in FIG. 4. In the data shown in FIG. 4, the striped bar indicates truncation from the 3' end of a 20mer anti-myc-luc antisense sequence defined by SEQ ID NO: 71 (see Table 3 below), and the solid bar represents truncation of the same sequence from its 5' end. Thus, for example, the striped bar 7mer sequence corresponds to SEQ ID NO:59, and the solid-bar 7mer, to SEQ ID NO:83. At reduced temperature of 30° C., PMO as short as 7 bases also caused significant inhibition (e.g. see FIG. 4 and Example 1), probably because the melting temperature ($T_m$) is between 30 and 37° C. for a 7 base PMO. However, beyond about 12-13 bases, there is a significant drop in the inhibition of protein translation observed. This behavior is contrary to the predicted behavior of oligonucleotide antisense compounds based on their ability to inhibit protein translation in either a bacterial or a eukaryotic cell free system, or in a mammalian-cell expression system, as will be seen below.

Figure 5:
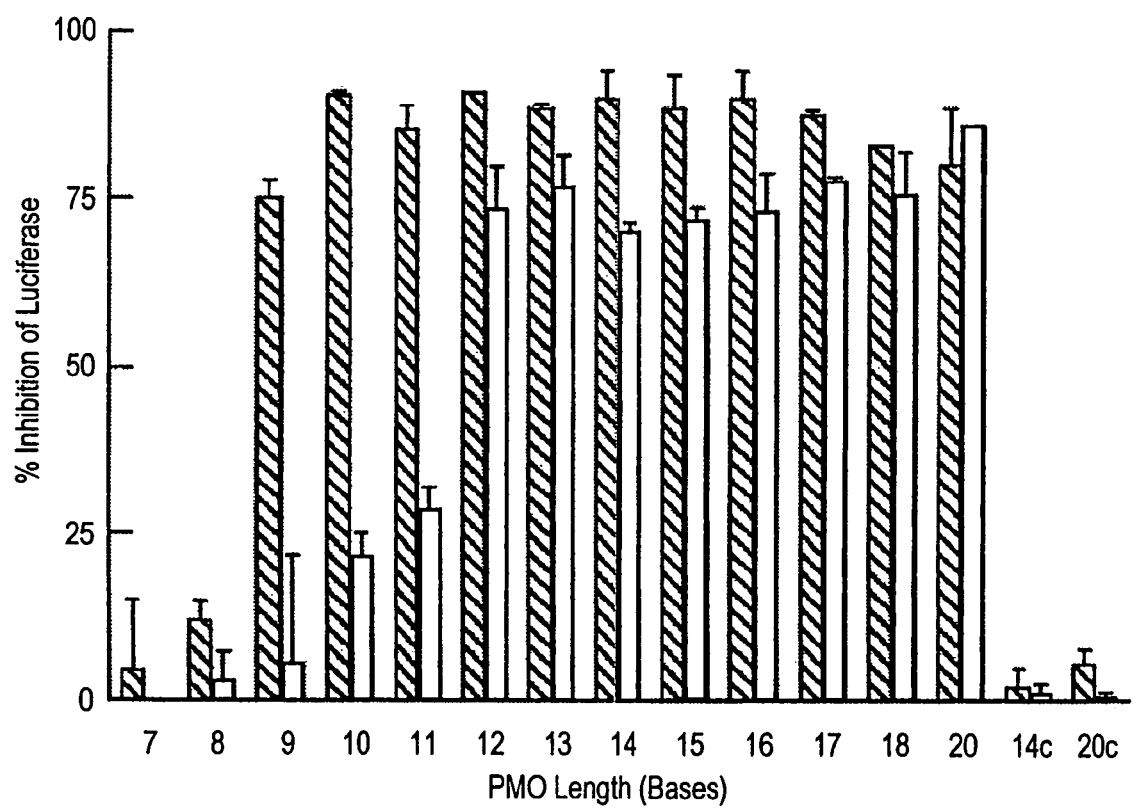
FIG. 5 shows the effect of antisense length on myc-luciferase expression in bacterial cell-free translation reactions. The same PMO used for the studies shown in FIG. 4 were added individually (100 nM) to bacterial cell-free protein synthesis reactions programmed to make myc-luc. Striped bars show 3' truncated PMO and solid bars show 5' truncated PMO.

The effect of antisense compound length in a bacterial cell-free expression system is shown in FIG. 5. The data show the degree of inhibition of the reporter gene by antisense sequences that have the indicated number of bases and that have been truncated at either the 5'-end (shaded bars) or 3' end (striped bars) of the 20-mer sequence defined below by ID NO:71. For sequences truncated at the 3' end, strong inhibition was seen for antisense compounds of lengths 9 up to 20, corresponding to sequences identified by SEQ ID NOS: 61 to 71. For sequences truncated at the 5' end, strong inhibition was seen for antisense compounds of lengths 12 up to 20, corresponding to sequences identified by SEQ ID NOS: 71 to 78. Unlike the inhibition studies reported in FIG. 4 for intact bacterial cells, the cell-free system data of FIG. 5 shows strong inhibition at antisense lengths up to 20 bases.

The data in FIG. 5 indicates a sequence positional effect as well as a sequence length effect for antisense inhibition in a cell-free system. To further examine this effect, PMO antisense compounds of length 10 and having the relative positions, with respect to the mRNA AUG start site, shown for the PMO numbers indicated in Table 3 below were examined in the same cell-free system. The data show that highest inhibition is achieved when the antisense sequence overlaps with the AUG start site (PMOs 358, 359, 360, 361, 362, and 363; SEQ ID NOS:93 to 98) or is downstream of the start site (PMOs 357, 356, and 208; SEQ ID NOS:92, 91 and 62, respectively). However, a decrease in inhibition is seen when the bulk of the bases are upstream of the start site (PMOs 331 and 364, SEQ ID NOS: 80 and 99). More generally, the antisense sequence should overlap the AUG start site of the target mRNA or be positioned within at least 10 bases of the start site.

Recent evidence suggests that peptide-PNA inhibited β-lactamase expression only when targeted to either the Shine-Dalgarno ribosome binding sequence (RBS) or the region around the start codon but not to anywhere else along the entire length of the mRNA (Dryselius, Aswasti et al. 2003). Results obtained in support of the present invention indicate that the RBS was not an effective target for PMO inhibition, at least for the myc-luc chimeric reporter gene, unlike the results observed for a PNA antisense compound.

Figure 11:
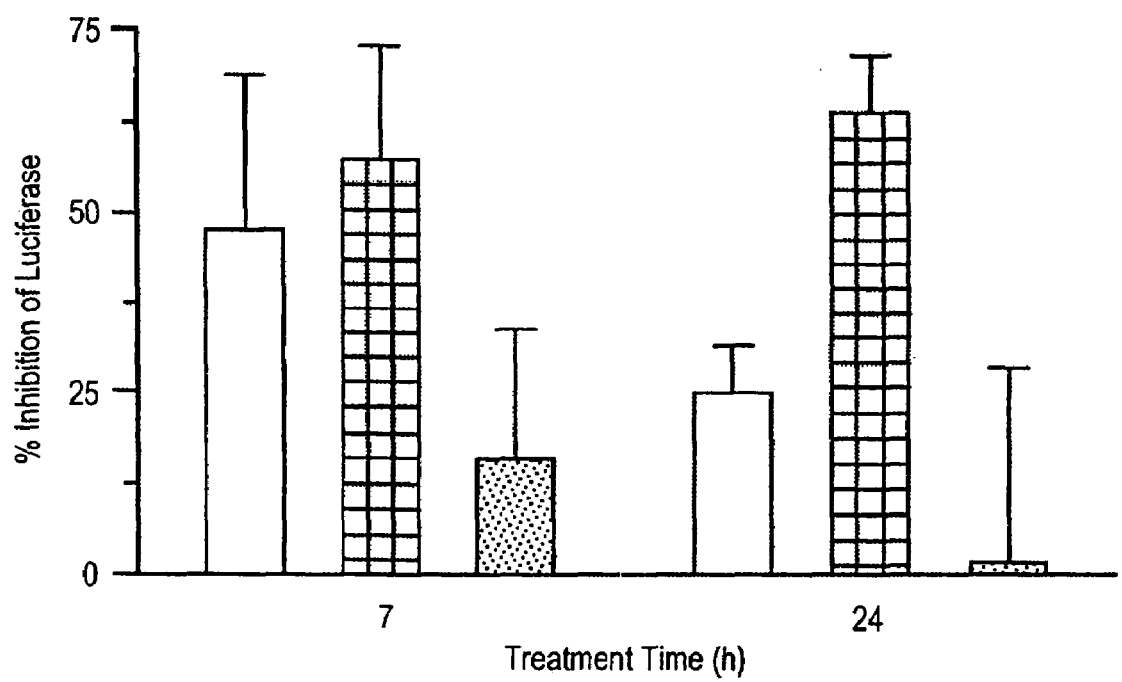
FIG. 11 shows the effect of antisense length on reporter gene expression in HeLa cells. Myc PMO 340 (11-base, open bars, SEQ ID NO:63), 126 (20-base, hatched bars, SEQ ID NO:71), or 143 (20-base nonsense sequence control, solid bars, SEQ ID NO:102) were loaded (10 µM) separately into HeLa cells that had been transfected with a myc-luc expression plasmid.
Figure 12:
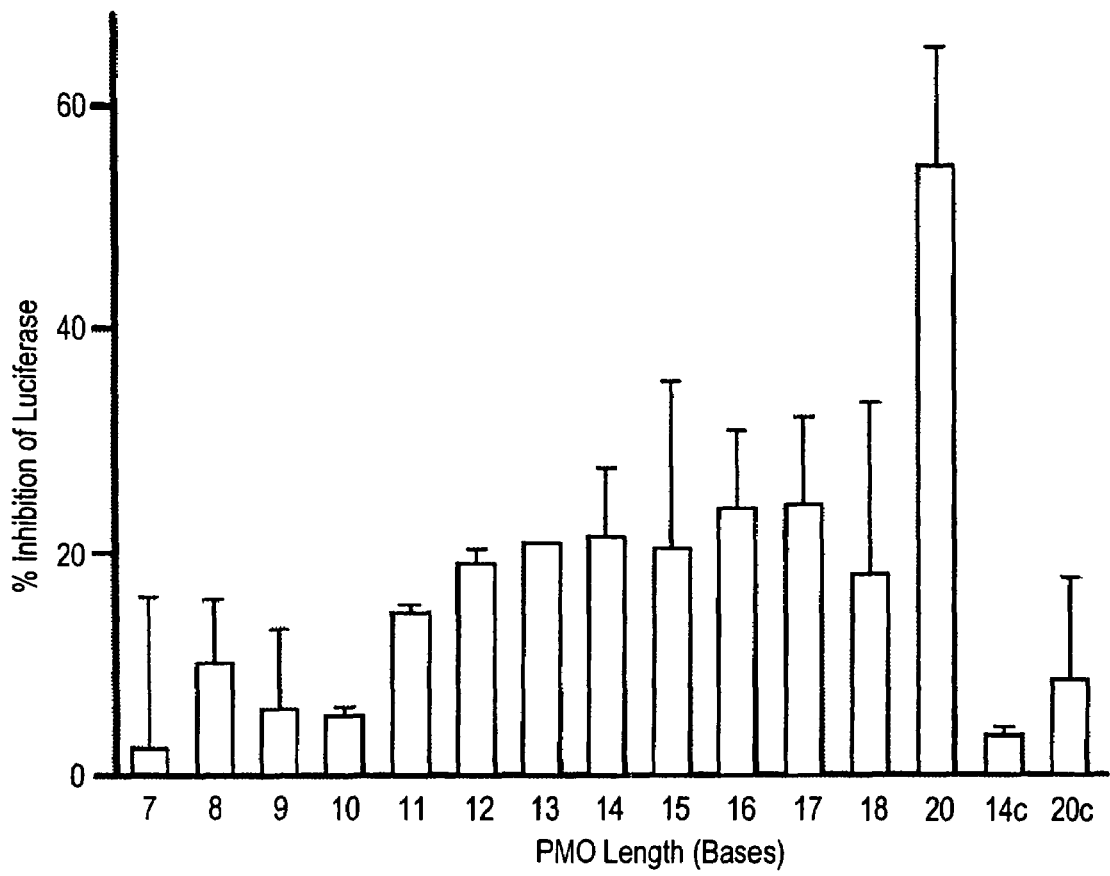
FIG. 12 shows rabbit reticulocyte cell-free translation with antisense of various lengths. The same 3' truncated PMO used for experiments shown in FIG. 1 were added individually (100 nM) to cell-free translation reactions composed of rabbit reticulocyte lysate and programmed to make myc-luc.

The results from FIG. 4 are also unpredictable from antisense inhibition effects observed in mammalian cells. Studies aimed at examining the effect of different length antisense compounds on inhibition of the myc-luc gene in Hela cells are described in Example 1 and shown in FIG. 11, where the open bars represent an 11mer compound, the cross-hatched bars, a 20 mer, and the solid bars, a nonsense sequence. Luciferase expression at 7 and 24 hours after exposure to the compound shows significantly greater inhibition by the larger antisense compound. Similarly, when the effect of antisense compound length was tested in a mammalian cell-free synthesis system (rabbit reticulocytes), inhibition increased successively from between about 10 to 17 bases, with very strong inhibition being observed for a 20mer compound, as seen in FIG. 12.

Figure 9A:
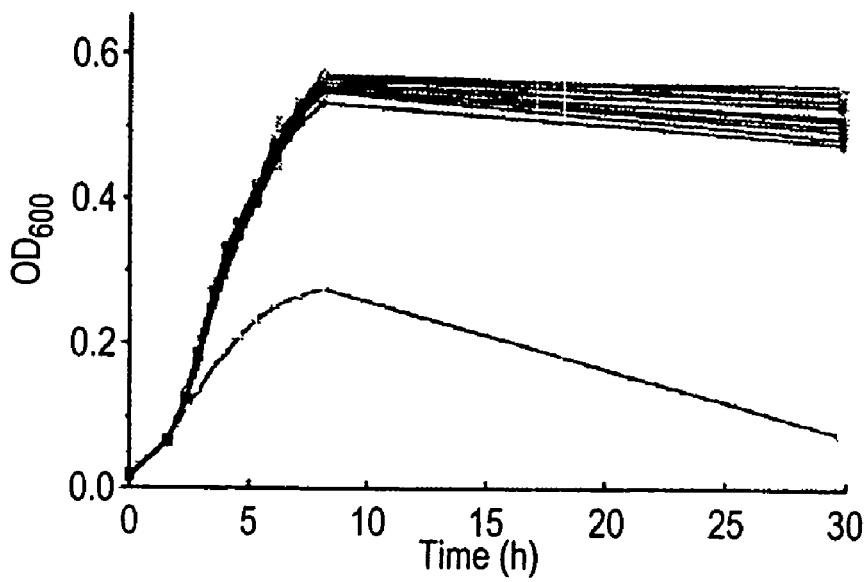
FIGS. 9A and 9B show the effect of AcpP antisense length on growth of E. coli AS19. Cultures of E. coli AS19 were grown (37° C.) with various lengths (6 to 20 bases) of overlapping PMO (20 µM) targeted to the region around the start codon of the E. coli acpP gene (Table 1, SEQ ID NO:2). Optical density (OD) was monitored over time (FIG. 9A) and open squares indicate culture with 11-base PMO 169 (SEQ ID NO:109) and viable cells measured after 8 hours (FIG. 9B).
Figure 9B:
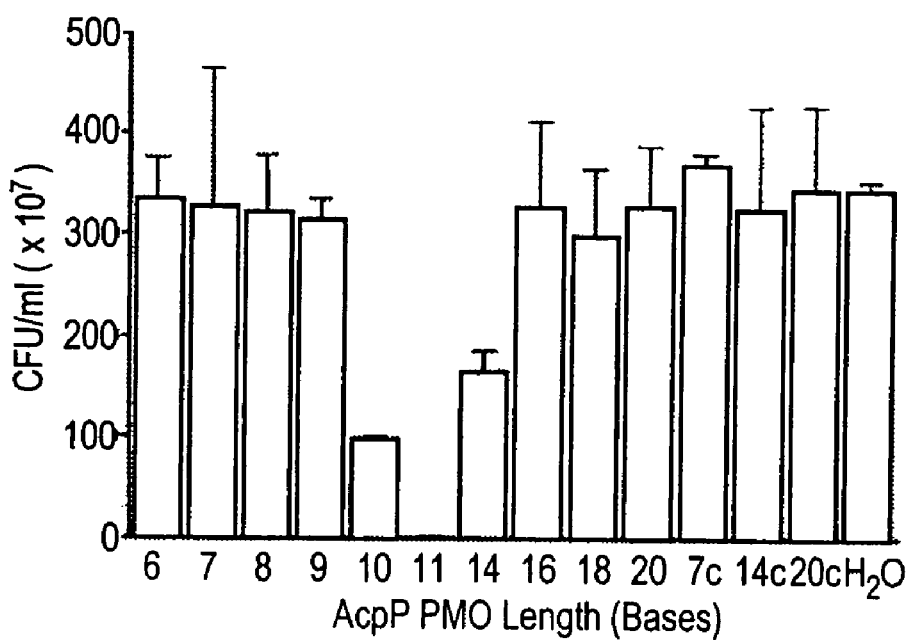
Figure 10:
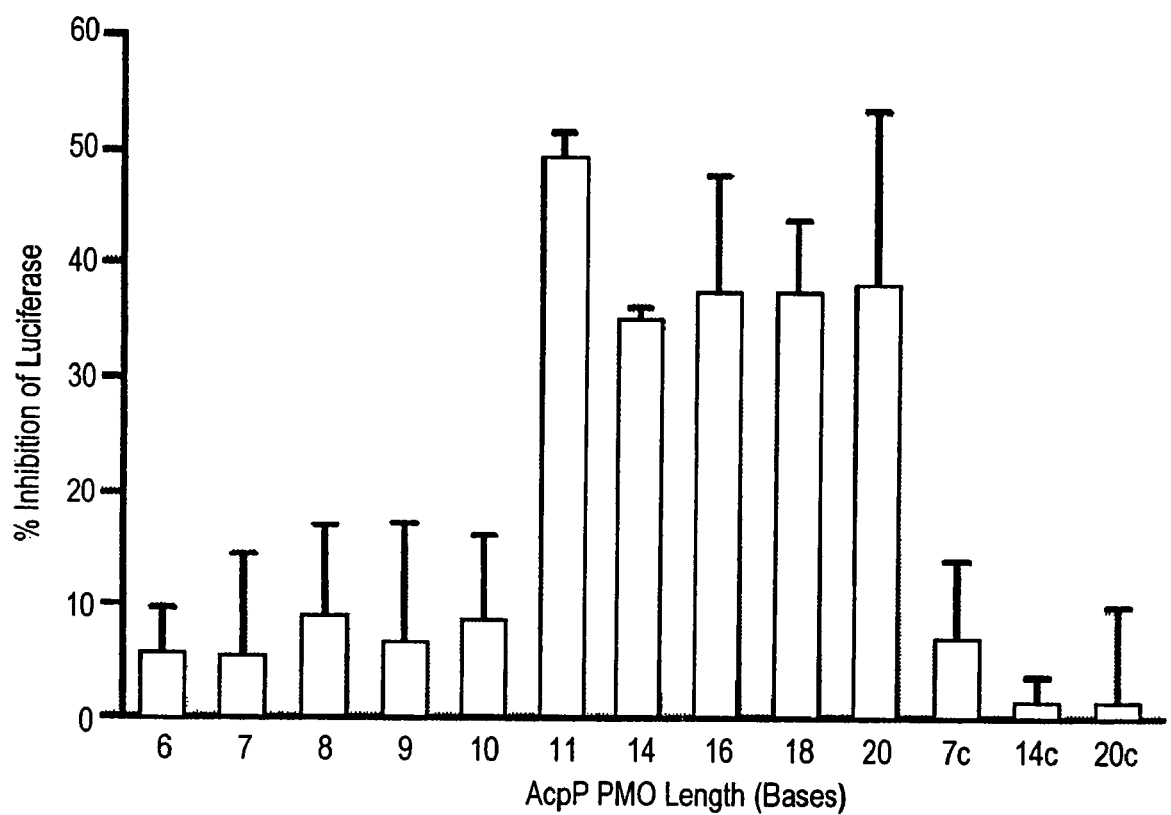
FIG. 10 shows the effect of antisense length on AcpP-luciferase expression in cell-free translation reactions. PMOs of various lengths and targeted around the start codon of E. coli acpP (Table 1) were added individually (100 nM) to bacterial cell-free translation reactions programmed to make Acp-luc.

To confirm that an oligomer antisense compound having relatively short lengths, e.g., 10-12 bases, gave optimal inhibition of a bacterial protein, antisense compounds directed against the AUG start site region of the bacterial AcpP gene were tested for their ability to inhibit bacterial growth in culture. These studies are reported in Example 2, with reference to FIGS. 9A and 9B. As seen in the latter figure, a striking inhibition was observed for antisense compounds having between 10 and 14 bases, with nearly complete inhibition being observed for the compound with an 11-base length. As with the expression studies involving marker genes described above, the results for inhibition of a bacterial gene in bacteria are unpredictable from the behavior of the same antisense compounds in a cell-free bacterial system. As seen in FIG. 10, strongest inhibition was observed between for antisense compounds between 11 and 20 bases.

Figure 8A:
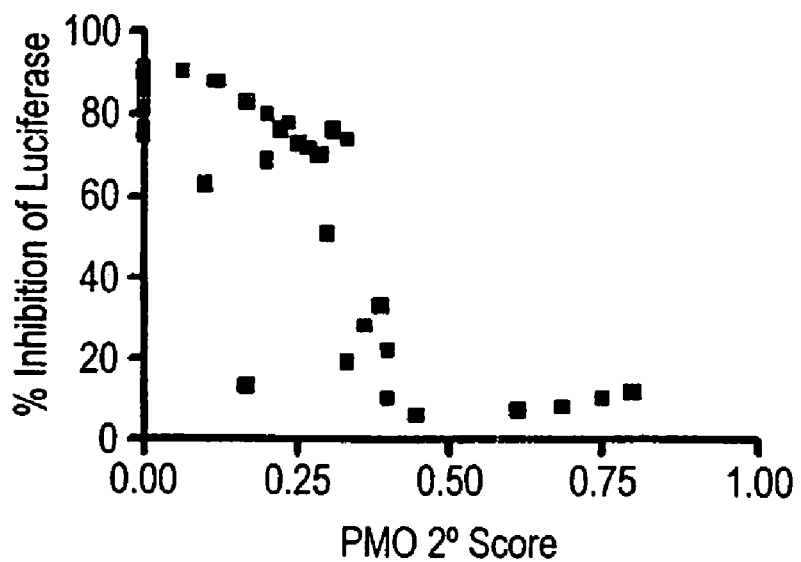
FIGS. 8A and 8B are correlation analyses comparing (8A) the inhibition of luciferase in cell-free reactions with the PMO 2° score and (8B) the same analysis on all 10-base PMO targeted to myc-luc.
Figure 8B:
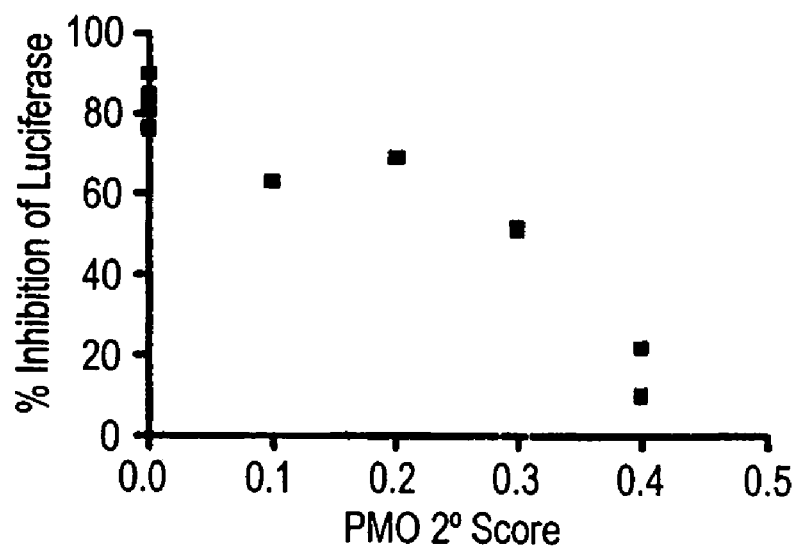

Other characteristics of the PMO were analyzed to detect a correlation with inhibition of myc-luc. The G plus C content of the PMO did not correlate with inhibition. However, a significant correlation between inhibition and theoretical secondary structure of the targeted region suggests that base pairing within the targeted region may reduce efficacy of the PMO (FIGS. 8A and 8B and Example 1). PMO targeted to sequences far downstream of the AUG start codon, significantly beyond 10 bases from the first base of the start codon, did not inhibit expression. Each of the downstream PMO targeted a different predicted secondary structure. One PMO (215, SEQ ID NO:101) was targeted to a region predicted to form a stem-like structure with 10 of its 11 bases paired with a contiguous stretch of complementary bases further downstream. The other downstream PMO (214, SEQ ID NO:100) was targeted to a region predicted to form a single-stranded region with all 11 of its bases unpaired. Target secondary structure does not appear to be a factor in the lack of efficacy of PMO targeted to sequences well downstream of the start codon.

Studies conducted in support of the present invention, and described below with respect to FIGS. 11 and 12, indicate that the antisense activity of short oligomer antisense compounds, relative to longer compounds, is also unpredictable from the antisense activity observed in eukaryotic systems. FIG. 11 shows the inhibition of luciferase expression (linked to the acpP gene) produced by a PMO that is 11 (open bars) or 20 (cross hatched bars) bases at 7 and 24 hours after exposure of cells to the antisense compound. As seen, substantially greater inhibition was seen with the 20mer antisense compound at both time points. The greater ability of longer oligomer antisense compounds to inhibit eukaryotic translation is also demonstrated by the study shown in FIG. 12. It is clear from this study that oligomeric compounds greater than 12 bases in length are more effective in inhibiting mRNA translation than those having a length between 10-12 bases.

Based on these considerations, exemplary targeting sequences for use in practicing the invention are those having between 10-14 bases, preferably complete, but at least 10-base complementarity with the mRNA target sequence, and complementary to a region of the mRNA that includes the AUG start site or a region up to 10 bases downstream of the start site. Where the compound of the invention is used in inhibiting infection by one of the bacteria identified in the table below, by inhibiting one of the three identified bacterial proteins, the antisense oligomer compound has a sequence that is complementary to at least 10 contiguous bases of the corresponding target sequence indicated in the table, where these target sequences are identified in the sequence listing below by SEQ ID NOS:1-58.

The antisense activity of the oligomer may be enhanced by using a mixture of uncharged and cationic phosphorodiamidate linkages as shown in FIGS. 2E and 2F. The total number of cationic linkages in the oligomer can vary from 1 to 6 and be interspersed throughout the oligomer. Preferably the number of charged linkages is at least 2 and no more than half the total backbone linkages, e.g., between 2-5 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

TABLE 2

Exemplary bacterial target regions

| Organism (GenBank Ref.) | Target Gene | Nucleotide Region | SEQ ID NO. |
|---|---|---|---|
| Escherichia coli (NC 000913) | ftsZ | 105295-105325 | 1 |
| | acpP | 1150828-1150858 | 2 |
| | gyrA | 2337422-2337452 | 3 |
| Escherichia coli 0157:H7 (NC 002655) | ftsZ | 109901-109931 | 4 |
| | acpP | 1595786-1595816 | 5 |
| | gyrA | 3136439-3136469 | 6 |
| Salmonella thyphimurium (NC 003197) | ftsZ | 155673-155703 | 7 |
| | acpP | 1280103-1280133 | 8 |
| | gyrA | 2376327-2376357 | 9 |
| Pseudomonas aeruginosa (NC 002516) | ftsZ | 4940463-4940493 | 10 |
| | acpP | 3325162-3325192 | 11 |
| | gyrA | 3559177-3559207 | 12 |
| Vibrio cholera (NC 002505) | ftsZ | 2566223-2566253 | 13 |
| | acpP | 254495-254525 | 14 |
| | gyrA | 1330197-1330227 | 15 |
| Neisseria gonorrhoea (NC 002946) | ftsZ | 1500031-1500060 | 16 |
| | acpP | 1724391-1724420 | 17 |
| | gyrA | 621170-621199 | 18 |
| Staphylococcus aureus (NC 002745) | ftsZ | 1165772-1165802 | 19 |
| | gyrA | 6995-7025 | 20 |
| | fmhB | 2322402-2322431 | 21 |
| Mycobacterium tuberculosis (NC 002755) | ftsZ | 2408265-2408295 | 22 |
| | acp | 1510172-1510202 | 23 |
| | gyrA | 7292-7322 | 24 |
| | pimA | 2935126-2935126 | 25 |
| | cysS2 | 4015924-4015953 | 26 |
| Helicobacter pylori (NC 000915) | ftsZ | 1042227-1042257 | 27 |
| | acp | 594253-594283 | 28 |
| | gyrA | 752502-752532 | 29 |
| Streptococcus pneumoniae (NC 003028) | ftsZ | 1566686-1566716 | 30 |
| | acp | 396681-396711 | 31 |
| | gyrA | 1149835-1149865 | 32 |
| Treponema palladium (NC 000919) | ftsZ | 414741-414771 | 33 |
| | acp | 877626-877656 | 34 |
| | gyrA | 4381-4411 | 35 |
| Chlamydia trachomatis (NC 000117) | acpP | 263915-263945 | 36 |
| | gyrA | 756474-756504 | 37 |
| Bartonella henselae (NC 005956) | ftsZ | 1232075-1232104 | 38 |
| | acp | 623133-623162 | 39 |
| | gyrA | 1123338-1123367 | 40 |
| Haemophilus influenzae (NC 000907) | ftsZ | 1212011-1212041 | 41 |
| | acp | 171140-171170 | 42 |
| | gyrA | 1344341-1344371 | 43 |
| Yersinia pestis (NC 003143) | ftsZ | 605864-605893 | 44 |
| | acp | 1824110-1824139 | 45 |
| | gyrA | 1370719-1370748 | 46 |
| Bacillus anthracis (NC 005945) | ftsZ | 3725338-3725367 | 47 |
| | acp | 3666877-3666906 | 48 |
| | gyrA | 6586-6615 | 49 |
| Burkholderia mallei (NC 006348) | ftsZ | 2650793-2650822 | 50 |
| | acp | 559420-559449 | 51 |
| | gyrA | 461883-461912 | 52 |
| Burkholderia pseudomallei (NC 006350) | ftsZ | 3600339-3600368 | 53 |
| | acp | 2945187-2945216 | 54 |
| | gyrA | 3039114-3039143 | 55 |

TABLE 2-continued

Exemplary bacterial target regions

| Organism (GenBank Ref.) | Target Gene | Nucleotide Region | SEQ ID NO. |
|---|---|---|---|
| Franciselia tulanensis (NC 006570) | ftsZ | 203738-203767 | 56 |
| | acp | 1421890-1421919 | 57 |
| | gyrA | 1639887-1639916 | 58 |

Any essential bacterial gene can be targeted using the methods of the present invention. As described above, an essential bacterial gene for any bacterial species can be determined using a variety of methods including those described by Gerdes for *E. coli* (Gerdes, Scholle et al. 2003). Many essential genes are conserved across the bacterial kingdom thereby providing additional guidance in target selection. Target regions can be obtained using readily available bioinformatics resources such as those maintained by the National Center for Biotechnology Information (NCBI). Complete reference genomic sequences for a large number of microbial species can be obtained (e.g., see www.ncbi.nlm.nih.gov/genomes/lproks.cgi) and sequences for essential bacterial genes identified. Bacterial strains can be obtained from the American Type Culture Collection (ATCC). Simple cell culture methods, such as those described in the Examples, using the appropriate culture medium and conditions for any given species, can be established to determine the antibacterial activity of antisense compounds.

The first step in selecting a suitable antisense selection is to identify, by the methods above, a targeting sequence that includes the AUG start site and/or contains at least about 10-20 bases downstream of the start site. Table 2 above gives the base-number locations of 30- to 31-base targeting sequences that span the AUG start site by about 10 bases on the upstream (5' side) and about 20 bases (including the start site) in the downstream coding region. The actual target sequences corresponding to these target-site locations are given in the sequence listing below, identified by SEQ ID NOS:1-58.

For purposes of illustration, assume that the antisense compound to be prepared is for use in inhibiting an *E. coli* bacterial infection in an individual infected with *E. coli* strain 0157:H7, and that the essential gene being targeted is the *E. coli* acpP gene. One suitable target sequence for this gene identified by the methods above is SEQ ID NO:2 having the sequence 5'-ATTTAAGAGTATGAGCACTATCGAA-GAACGC-3' where the sequence gives the DNA thymine (T) bases rather than the RNA uracil (U) bases, and where the AUG start site (ATG) is shown in bold.

Again, for purposes of illustration, four model antisense targeting sequence, each of them 11 bases in length, are selected: (i) an antisense sequence that spans the AUG start site with four bases of each side and has the sequence identified by SEQ ID NO:126; (ii) an antisense sequence that overlaps the AUG starts at its '5 end and extends in a 3' direction an additional 8 bases into the coding region of the gene, identified as SEQ ID NO:127; (iii) an antisense sequence complementary to bases 5-15 of the gene's coding region, identified as SEQ ID NO:109, and (iv) an antisense sequence complementary to bases 11-21 of the gene's coding region, identified as SEQ ID NO:128. These sequences are listed in Table 3 below.

Once antisense sequences have been selected and the antisense compound synthesized, the compounds may be tested for ability to inhibit bacterial growth, in this case growth of an *E. coli* strain in culture. Following the protocol in Example 2, for example, the four 11mer sequences described above are individually tested for optimal activity, e.g., maximum drop in CFU/ml at a given dose, e.g., 5-20 μM, against an *E. coli* culture. Compound(s) showing optimal activity are then tested in animal models, as described in Example 3, or veterinary animals, prior to use for treating human infection.

TABLE 3

PMO Sequences for the *E coli* acpP protein

| Sequence (5' to 3') | Target | SEQ ID NO |
|---|---|---|
| TGC TCA TAC TC | *E coli* acpP | 126 |
| ATA GTG CTC AT | *E coli* acpP | 127 |
| CTT CGA TAG TG | *E coli* acpP | 109 |
| CG TTC TTC CG | *E coli* acpP | 128 |

IV. Method for Inhibiting Bacteria

In one aspect, the invention includes a method of inhibiting bacterial infection, by exposing the infecting bacteria to a 10-12 base oligomeric antisense compound of the type characterized above. This general method is demonstrated by the study reported in Example 2 and described above with respect to FIG. 9.

Figure 13:
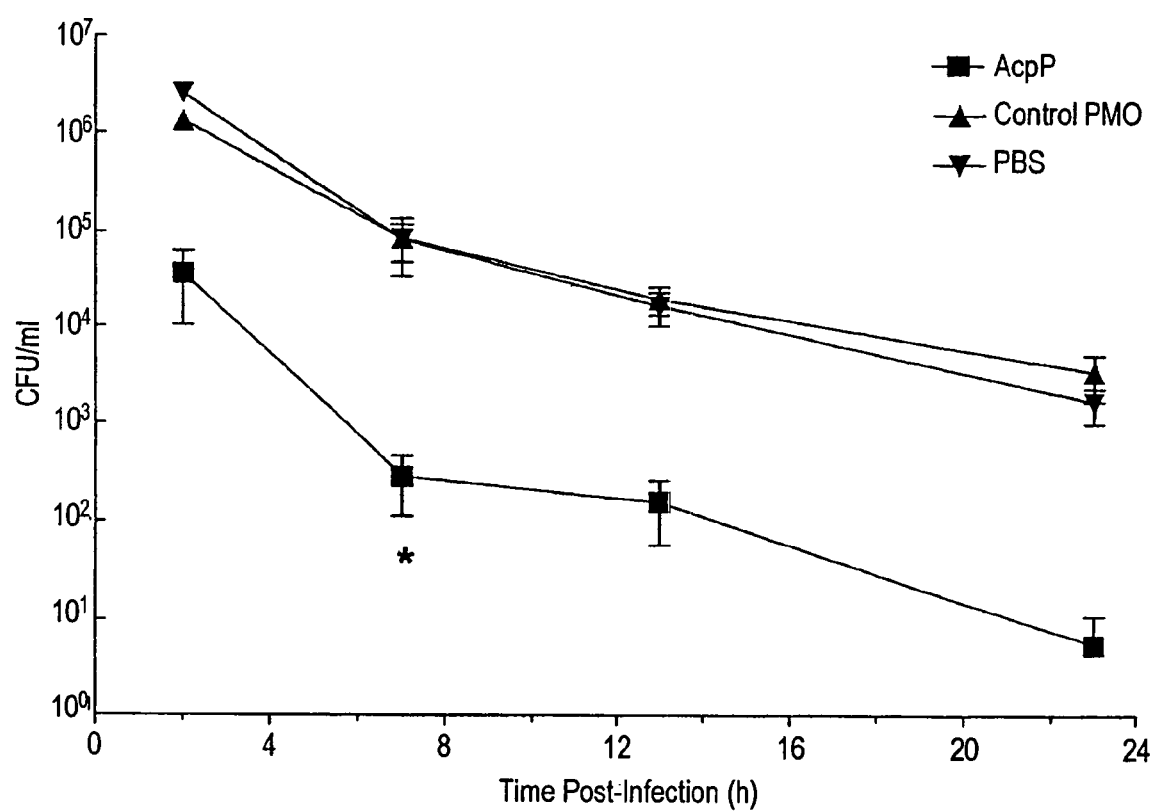
FIG. 13 shows CFU/ml in peritoneal lavages from mice infected with permeable E. coli strain AS19 and treated with acpP PMO (■), nonsense PMO (▲), or PBS (▼) at 0 h. At each time indicated, peritoneal lavage was collected and analyzed for bacteria (CFU/ml) from 3 mice in each treatment group.

In one aspect, the method is applied to inhibiting a bacterial infection in a mammalian subject, including a human subject, by administering the antisense compound to the subject in a therapeutic amount. To demonstrate the method, groups of 4 mice were injected IP with *E. coli* AS19, which has a genetic defect that makes it abnormally permeable to high MW solutes. Immediately following infection, each mouse was injected IP with 300 μg of an 11-base PMO complementary to acpP, an 11-base nonsense sequence PMO, or PBS, as detailed in Example 3. As seen in FIG. 13, mice treated with the target antisense showed a reduction in bacterial CFUs of about 600 at 23 h, compared with control treatment.

Figure 14:
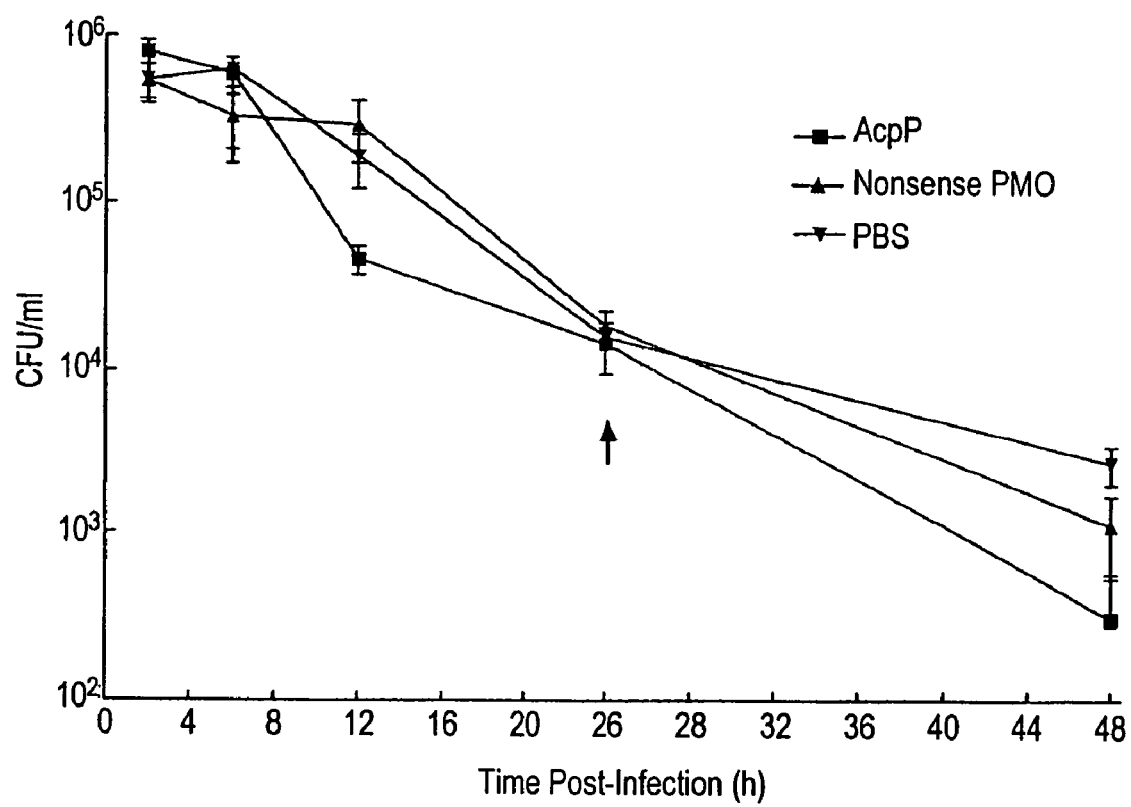
FIG. 14 shows CFU/ml in peritoneal lavages from mice infected with E. coli strain SM105 and treated with PMO as described in FIG. 13.

The same PMOs were again tested, except with *E. coli* SM105, which has a normal outer membrane. In this method, anti-acpP PMO reduced CFU by 84% compared to nonsense PMO at 12 h post-infection. There was no reduction of CFU at 2, 6, or 24 h (FIG. 14). Mice were injected with a second dose at 24 h post-infection. By 48 h post-infection the CFU of acpP PMO-treated mice were 70% lower than the CFU of nonsense PMO-treated mice (FIG. 14).

To demonstrate that the effect on bacterial infection was sequence specific, a luciferase reporter gene whose expression would not affect growth was used, and luciferase expression was measured directly by two independent criteria, luciferase activity and luciferase protein abundance. As detailed in Example 3, the study demonstrated that an antisense compound complementary to the luciferase mRNA inhibited luciferase expression at two different times after administration of the PMO. Moreover, inhibition was quantitatively similar with both methods of measurement. These results show directly that PMO inhibit bacterial target gene expression in vivo in a sequence-specific manner.

It will be understood that the in vivo efficacy of such an antisense oligomer in a subject using the methods of the invention is dependent upon numerous factors including, but not limited to, (1) the target sequence; (2) the duration, dose and frequency of antisense administration; and (3) the general condition of the subject.

In another embodiment of the invention, the antisense oligonucleotides of the invention find utility in the preparation of anti-bacterial vaccines. In this aspect of the invention, a culture of a particular type of bacteria is incubated in the presence of a morpholino-based antisense oligomer of the type described above, in an amount effective to produce replication-crippled and/or morphologically abnormal bacterial cells. Such replication-crippled and/or morphologically abnormal bacterial cells are administered to a subject and act as a vaccine.

The efficacy of an in vivo administered antisense oligomer of the invention in inhibiting or eliminating the growth of one or more types of bacteria may be determined by in vitro culture or microscopic examination of a biological sample (tissue, blood, etc.) taken from a subject prior to, during and subsequent to administration of the antisense oligomer. (See, for example, Pari, G. S. et al., *Antimicrob. Agents and Chemotherapy* 39(5):1157-1161, 1995; Anderson, K. P. et al., *Antimicrob. Agents and Chemotherapy* 40(9):2004-2011, 1996.) The efficacy of an in vivo administered vaccine of antisense oligomer-treated bacteria may be determined by standard immunological techniques for detection of an immune response, e.g., ELISA, Western blot, radioimmunoassay (RIA), mixed lymphoctye reaction (MLR), assay for bacteria—specific cytotoxic T lymphocytes (CTL), etc.

A. Administration Methods

Effective delivery of the antisense oligomer to the target nucleic acid is an important aspect of treatment. In accordance with the invention, such routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a bacterial infection of the skin is topical delivery, while delivery of an antisense oligomer in the treatment of a bacterial respiratory infection is by inhalation. Methods effective to deliver the oligomer to the site of bacterial infection or to introduce the oligonucleotide into the bloodstream are also contemplated.

Transdermal delivery of antisense oligomers may be accomplished by use of a pharmaceutically acceptable carrier adapted for e.g., topical administration. One example of morpholino oligomer delivery is described in PCT patent application WO 97/40854, incorporated herein by reference.

In one preferred embodiment, the oligomer is a morpholino oligomer, contained in a pharmaceutically acceptable carrier, and is delivered orally.

The antisense oligonucleotide may be administered in any convenient vehicle which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of the antisense oligonucleotide into cells. (See, e.g., Williams, S. A., *Leukemia* 10(12):1980-1989, 1996; Lappalainen et al., *Antiviral Res.* 23:119, 1994; Uhlmann et al., ANTISENSE OLIGONUCLEOTIDES: A NEW THERAPEUTIC PRINCIPLES, *Chemical Reviews*, Volume 90, No. 4, pages 544-584, 1990; Gregoriadis, G., Chapter 14, Liposomes, *Drug Carriers in Biology and Medicine*, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., *J. Biol. Chem.* 262:4429-4432, 1987.)

Sustained release compositions are also contemplated within the scope of this application. These may include semipermeable polymeric matrices in the form of shaped articles such as films or microcapsules.

Typically, one or more doses of antisense oligomer are administered, generally at regular intervals for a period of about one to two weeks. Preferred doses for oral administration are from about 10 mg oligomer/patient to about 250 mg oligomer/patient (based on a weight of 70 kg). In some cases, doses of greater than 250 mg oligomer/patient may be necessary. For IV administration, the preferred doses are from about 1.0 mg oligomer/patient to about 100 mg oligomer/patient (based on an adult weight of 70 kg). The antisense compound is generally administered in an amount and manner effective to result in a peak blood concentration of at least 200-400 nM antisense oligomer.

In a further aspect of this embodiment, a morpholino antisense oligonucleotide is administered at regular intervals for a short time period, e.g., daily for two weeks or less. However, in some cases the antisense oligomer is administered intermittently over a longer period of time. Administration of a morpholino antisense oligomer to a subject may also be followed by, or concurrent with, administration of an antibiotic or other therapeutic treatment.

In one aspect of the method, the subject is a human subject, e.g., a patient diagnosed as having a localized or systemic bacterial infection. The condition of a patient may also dictate prophylactic administration of an antisense oligomer of the invention or an antisense oligomer treated bacterial vaccine, e.g. in the case of a patient who (1) is immunocompromised; (2) is a burn victim; (3) has an indwelling catheter; or (4) is about to undergo or has recently undergone surgery.

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antibacterial antisense compound of the type described above. Also contemplated is in a method of feeding livestock and poultry with a food grain supplemented with subtherapeutic levels of an antibiotic, an improvement in which the food grain is supplemented with a subtherapeutic amount of an antibacterial oligonucleotide composition as described above.

The methods of the invention are applicable, in general, to treatment of any condition wherein inhibiting or eliminating the growth of bacteria would be effective to result in an improved therapeutic outcome for the subject under treatment.

One aspect of the invention is a method for treatment of a bacterial infection which includes the administration of a morpholino antisense oligomer to a subject, followed by or concurrent with administration of an antibiotic or other therapeutic treatment to the subject.

B. Treatment Monitoring Methods

It will be understood that an effective in vivo treatment regimen using the antisense oligonucleotide compounds of the invention will vary according to the frequency and route of administration, as well as the condition of the subject under treatment (i.e., prophylactic administration versus administration in response to localized or systemic infection). Accordingly, such in vivo therapy may benefit from monitoring by tests appropriate to the particular type of bacterial infection under treatment and a corresponding adjustment in the dose or treatment regimen in order to achieve an optimal therapeutic outcome.

The efficacy of a given therapeutic regimen involving the methods described herein may be monitored, e.g., by general indicators of infection, such as complete blood count (CBC), nucleic acid detection methods, immunodiagnostic tests, or bacterial culture.

Identification and monitoring of bacterial infection generally involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses (i.e., oxidase, catalase positive for *Pseudomonas aeruginosa*), and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The antisense oligomer treatment regimen may be adjusted (dose, frequency, route, etc.), as indicated, based on the results of immunoassays, other biochemical tests and physiological examination of the subject under treatment.

From the foregoing, it will be appreciated how various objects and features of the invention are met. The method provides an improvement in therapy against bacterial infection, using relatively short antisense sequences to achieve enhanced cell uptake and anti-bacterial action. As a result, drug therapy is more effective and less expensive, both in terms of cost and amount of compound required.

An important advantage of the invention is that compounds effective against virtually any pathogenic bacterium can be readily designed and tested, e.g., for rapid response against new drug-resistant bacteria, or in cases of bioterrorism. Once a target bacterium is identified, the sequence selection methods described allow one to readily identify one or more likely gene targets, among a number of essential genes, and prepare antisense compounds directed against the identified target. Because clinical testing on the safety and efficacy, once established for a small group of compounds, can be extrapolated to virtually any new target, relatively little time is needed in addressing new bacterial-infection challenges as they arise.

The following examples are intended to illustrate but not to limit the invention.

Materials and Methods

Phosphorodiamidate Morpholino Oligomers.

PMO were synthesized and purified at AVI BioPharma, Inc. (Corvallis, Oreg.) as previously described (Geller, Deere et al. 2003, Summerton and Weller, 1997), dissolved in water, filtered through a 0.2 µM membrane (HT Tuffryn®, Gelman Sciences, Inc., Ann Arbor, Mich.), and stored at 4° C. Sequences of PMO used in this study are shown in Table 3. The concentration of PMO was determined spectrophotometrically by measuring the absorbance at 260 nm and calculating the molarity using the appropriate extinction coefficient.

Figure 15:
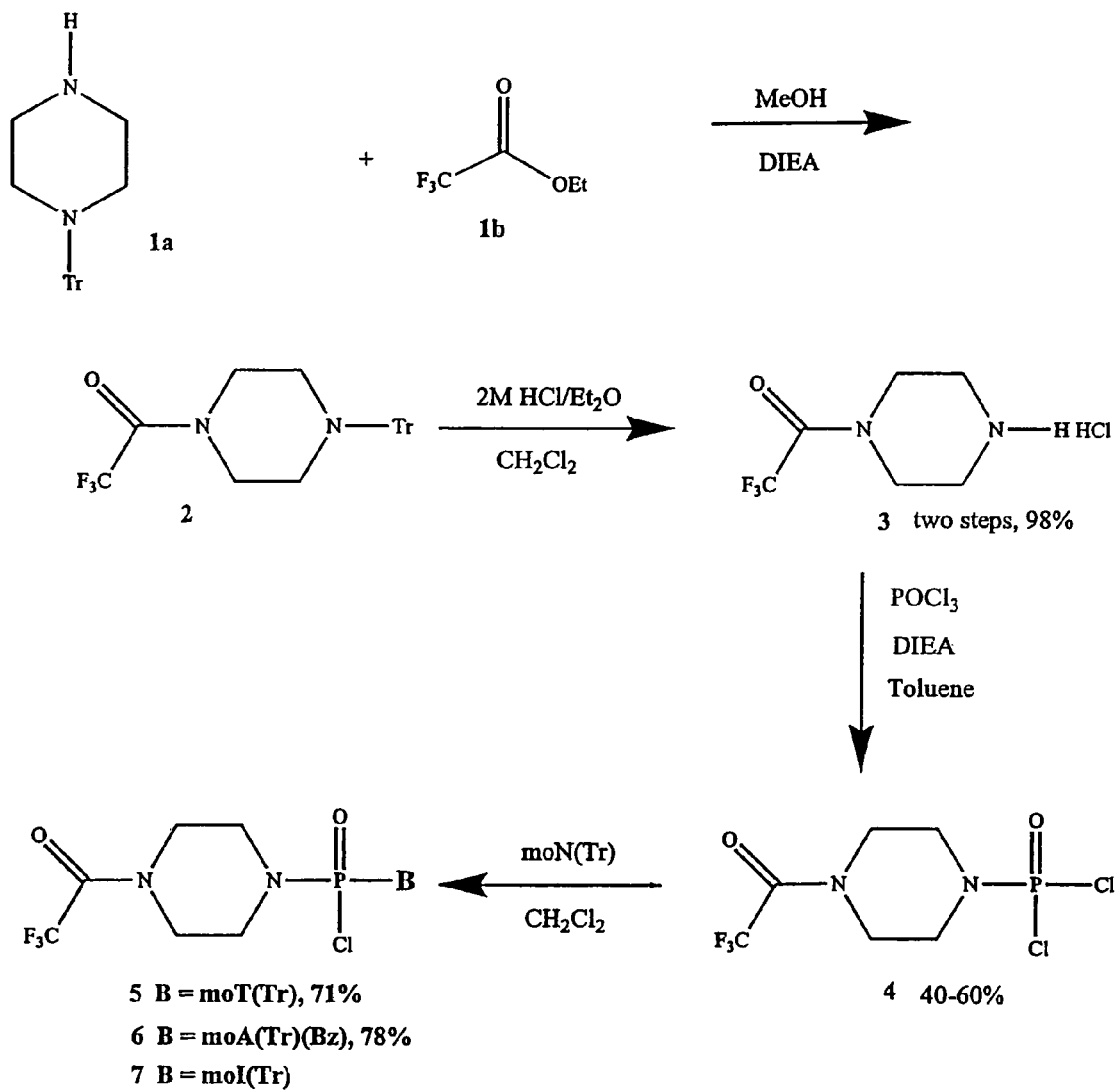
FIG. 15 shows the synthetic steps to produce subunits used to produce +PMO containing the (1-piperazino) phosphinylideneoxy cationic linkage as shown in FIG. 2F.

A schematic of a synthetic pathway that can be used to make morpholino subunits containing a (1 piperazino) phosphinylideneoxy linkage is shown in FIG. 15; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5,6,7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

Bacteria and Growth Conditions

Bacterial strains were obtained from the American Type Culture Collection (ATCC) or the *E. coli* Genetic Stock Center at Yale University. All pure culture experiments were done in 96-well plates. OD600 readings and plating of cells for CFU/ml determinations were done in triplicate.

*Escherichia coli* AS19 and SM101, which have defects in lipopolysaccharide synthesis that result in outer membrane permeability to high MW solutes, were grown aerobically in LB broth at 37° C., and 30° C., respectively. Transformants that expressed pSE380myc-luc were grown in LB plus 100 µg/ml ampicillin.

*E. coli* AS19 and SM105 were grown in LB broth (supplemented with 100 µg/ml ampicillin for transformants that expressed luciferase) to $OD_{600}=0.12$, centrifuged (4,000×g, 10 min, 20° C.), and resuspended in 5% mucin (type II, Sigma Chemical Co., St. Louis,)/PBS to final concentrations as follows: AS19, $1.5 \times 10^8$ CFU/ml; SM105, $5.7 \times 10^7$ CFU/ml; AS19 (pT7myc-luc), $7.2 \times 10^9$ CFU/ml.

Reporter Gene.

Standard molecular biology procedures were used for all constructions. All constructs were sequenced. Two reporter systems (pT7myc-luc and pSE380myc-luc) for antisense inhibition were previously constructed as described (Geller, Deere et al. 2003) by fusing 30 bp of the 5' end of human c-myc to all but the start codon of the gene for luciferase (luc). The constructs were separately transformed into *E. coli* SM101 and AS19.

The acpP-luc reporter (pCNacpP-luc) was made by ligating a SalI-NotI restriction fragment of luc with the SalI-NotI fragment of pCiNeo (Promega Corp., Madison, Wis.), removing the adenosine from the start codon by site-directed mutagenesis, then directionally cloning a synthetic fragment of acpP (bp −17 to +23, inclusive, where +1 is adenosine of the start codon) between the NheI-SalI sites. pCNmyc-luc was made in the same way, except myc sequence from −14 through +16, inclusive (numbering adenosine of the start codon as +1) instead of acpP was cloned into the NheI-SalI sites. Luciferase enzyme activity was measured in bacteria as described (Geller, Deere et al. 2003).

Cell-Free Protein Synthesis

Bacterial, cell-free protein synthesis reactions were performed by mixing reactants on ice according to the manufacturer's instruction (Promega Corp.). Reactions were programmed with either pT7myc-luc plasmid in a coupled transcription/translation reaction, or with mRNA synthesized in a cell-free RNA synthesis reaction (Ambion, Inc., Austin, Tex., MEGAscript T7 High Yield Transcription Kit) programmed with pT7myc-luc. All acp-luc reactions were programmed with pCNacpP-luc. Where indicated, cell-free reactions were composed with rabbit reticulocyte lysate as described by the manufacturer (Promega Corp.). PMO was added to a final concentration of either 100 nM or 200 nM as indicated. After 1 h at 37° C., the reactions were cooled on ice and luciferase was measured as described (Geller, Deere et al. 2003).

Mammalian Tissue Culture

HeLa cells were transfected in T75 tissue culture flasks (Nalge Nunc, Inc., Rochester, N.Y.) with a luciferase reporter plasmid (pCNmyc-luc) using Lipofectamine Reagent (Gibco BRL, Grand Island, N.Y.,) according to user's manual in serum-free media (Gibco, Inc., Carlsbad, Calif., Opti-MEM1) for 5 hours before re-addition of growth medium (Hyclone, Inc., Logan, Utah, HyQ DME/F12 supplemented with 10% Fetal Bovine Serum and Gibco Antibiotic-Antimycotic 15240-062) at 37° C. in 5% $CO_2$. After 24 hours, the cells were pooled and $1\times10^6$ was added to each well of a 6-well plate (BD Biosciences, San Jose, Calif.) in 2 ml of growth media. After an additional 24 hours, PMO was added to a final concentration of 10 µM in 2 ml fresh growth media and the cells were scraped from the plate surface with a rubber policeman to deliver the PMO to the cell as previously described (Partridge, Vincent et al. 1996). After scrape-loading, the cells were transferred to fresh 6-well plates and incubated at 37° C. until the time of assay. At 7 and 24 hours the cells were examined by microscopy to verify that each culture had the same number of cells, harvested by centrifugation, and lysed in Promega Cell Culture Lysis Reagent (Promega Corp.). Luciferase was measured by mixing the cell lysate with Luciferase Assay Reagent (Promega Corp.) and reading light emission in a Model TD-20e luminometer (Turner Designs, Inc., Mountain View, Calif.).

RNA Secondary Structure

The RNA folding algorithm M-Fold© (Zuker 2003) was used to predict the secondary structure of bases 1-120 or 90-1745 of the mRNA transcribed from pT7myc-luc. The folded structure of bases 1-120 had a minimum $\Delta G=-6.5$ kcal/mol, and that of bases 90-1745 was $\Delta G=-452.28$ kcal/mol. Each PMO was scored (referred to as 2° score) by calculating the fraction of bases (in the PMO) that are complementary to double stranded (duplex) regions within the folded target mRNA. For example, PMO 331 (Table 4, SEQ ID NO:80) is 10 bases in length and complementary to a region of myc-luc mRNA that, according to M-Fold prediction, forms duplex RNA at 4 of its 10 bases (the other 6 bases are not paired). The 2° score for PMO 331 would therefore be 4 bases/10 bases=0.400.

Animals

Female, 6 to 8 week old Swiss Webster mice (Simonsen Labs, Inc., Gilroy, Calif.) were used in all but one experiment, but identical results were obtained with males. Infection was established as described in (Frimodt-Moller, Knudsen et al. 1999). Each mouse was injected IP with 0.1 ml of bacteria resuspended in 5% mucin/PBS, then immediately injected IP with 0.1 ml of PMO (3.0 mg/ml) or PBS. At various times after infection (as indicated in the figures), groups (n=3 to 5) of mice were injected IP with 2.0 ml PBS, and their abdomens gently massaged for 2 min. Peritoneal lavage was removed and stored on ice for ~1 h. The lavages were diluted in PBS and plated in triplicate on LB to determine CFU.

Luciferase and Western Blot

Peritoneal ravages (1.00 ml) from mice infected with AS19 (pT7myc-luc) were centrifuged (10,000×g, 2 min, 4° C.) and the supernatants discarded. The pellets were resuspended in 50 µl PBS. An aliquot of resuspended cells was mixed with an equal volume of 2× cell culture lysis reagent (Promega, Inc., Madison, Wis.) and frozen at −85° C. Frozen lysates were thawed and luciferase light production was measured in duplicate in a luminometer as described (Geller, Deere et al. 2003). A second aliquot of the cell suspension was mixed with 2× SDS sample buffer and analyzed by western blot using 4-20% gradient Gene Mate Express Gels (ISC BioExpress, Inc., Kaysville, Utah). Blots were prepared with primary antibody to luciferase (Cortex Biochmical, San Leandro, Calif.) or antisera to OmpA (Geller and Green 1989), secondary goat anti-rabbit IgG-horse radish peroxidase conjugate (Santa Cruz Biotechnology, Inc., Santa, Cruz, Calif.), and ECL Western Blotting Reagent (Amersham Biosciences, Buckinghamshire, England). Film negatives were scanned and digitized on a Kodak Image Station 440 CF. The net intensity of each band was calculated by subtracting the mean background intensity. Luciferase protein was normalized to OmpA by dividing the net intensity of the luciferase band by the net intensity of the OmpA band in the same sample. The % inhibition was calculated by subtracting the mean luciferase/OmpA of luc PMO-treated mice from mean luciferase/OmpA of nonsense PMO-treated mice, dividing the difference by mean luciferase/OmpA of nonsense PMO-treated mice, then multiplying by 100%.

Statistical Analysis

Spearman's rank-order correlation was used to analyze correlations between the inhibitory effects of PMO and either G+C content or secondary structure score of each PMO. The one-tailed, non-parametric Mann-Whitney test was used to analyze treatment group means.

Oligomer Sequences

Exemplary targeting oligomers used in describing the present invention are listed below in Table 4. The listed oligomers all target *E. coli*, the experimental bacterial strain used in experiments in support of the invention.

TABLE 4

PMO Sequences

| PMO Sequence (5' to 3') | % GC | 2° Score | Target | SEQ ID NO |
|---|---|---|---|---|
| 328 ACG TTG A | 43 | 0 | myc-luc | 59 |
| 327 ACG TTG AG | 50 | 0 | myc-luc | 60 |
| 326 ACG TTG AGG | 56 | 0 | myc-luc | 61 |
| 208 ACG TTG AGG G | 60 | 0 | myc-luc | 62 |
| 340 ACG TTG AGG GG | 64 | 0 | myc-luc | 63 |
| 298 ACG TTG AGG GGC | 67 | 0 | myc-luc | 64 |
| 250 ACG TTG AGG GGC A | 62 | 0 | myc-luc | 65 |
| 249 ACG TTG AGG GGC AT[3] | 57 | 0 | myc-luc | 66 |
| 248 ACG TTG AGG GGC ATC | 60 | 0 | myc-luc | 67 |
| 247 ACG TTG AGG GGC ATC G | 62 | .0625 | myc-luc | 68 |
| 246 ACG TTG AGG GGC ATC GT | 59 | .1176 | myc-luc | 69 |
| 245 ACG TTG AGG GGC ATC GTC | 61 | .1667 | myc-luc | 70 |
| 126 ACG TTG AGG GGC ATC GTC | 65 | .2000 | myc-luc | 71 |
| 239 G TTG AGG GGC ATC GTC GC | 67 | .2222 | myc-luc | 72 |
| 240 TTG AGG GGC ATC GTC GC | 65 | .2353 | myc-luc | 73 |
| 241 TG AGG GGC ATC GTC GC | 69 | .2500 | myc-luc | 74 |
| 242 G AGG GGC ATC GTC GC | 73 | .2667 | myc-luc | 75 |
| 243 AGG GGC ATC GTC GC | 71 | .2857 | myc-luc | 76 |
| 244 GG GGC ATC GTC GC | 77 | .3077 | myc-luc | 77 |
| 329 G GGC ATC GTC GC | 75 | .3333 | myc-luc | 78 |
| 330 GGC ATC GTC GC | 73 | .3636 | myc-luc | 79 |
| 331 GC ATC GTC GC | 70 | .4000 | myc-luc | 80 |
| 332 C ATC GTC GC | 67 | .4444 | myc-luc | 81 |
| 333 ATC GTC GC | 62 | NC[4] | myc-luc | 82 |
| 334 TC GTC GC | 71 | NC | myc-luc | 83 |
| 341 GGA AAC CGT TGT GGT CTC | 60 | .7500 | myc-luc 5' | 84 |
| 342 AC CGT TGT GGT CTC CC | 62 | .6875 | myc-luc 5' | 85 |
| 343 GT TGT GGT CTC CC | 69 | .6154 | myc-luc 5' | 86 |
| 344 GT GGT CTC CC | 70 | .8000 | myc-luc 5' | 87 |
| 345 CGT CGC GGG ATT CCT TCT | 61 | .3889 | RBS & 3' of | 88 |
| 346 AAA GTT AAA CAA AAT TAT | 11 | .1667 | 5' of RBS | 89 |
| 347 TCC TTC TTA AAG TTA AAC | 28 | .3333 | RBS & 5'of | 90 |
| 356 CGT TGA GGG G | 70 | 0 | myc-luc | 91 |
| 357 GT TGA GGG GC | 70 | 0 | myc-luc | 92 |
| 358 T TGA GGG GCA | 60 | 0 | myc-luc | 93 |
| 359 TGA GGG GCA T | 60 | 0 | myc-luc | 94 |
| 360 GA GGG GCA TC | 70 | 0 | myc-luc | 95 |
| 361 A GGG GCA TCG | 70 | .1000 | myc-luc | 96 |
| 362 GGG GCA TCG T | 70 | .2000 | myc-luc | 97 |
| 363 GG GCA TCG TC | 70 | .3000 | myc-luc | 98 |
| 364 G GCA TCG TCG | 70 | .4000 | myc-luc | 99 |
| 214 AAT AGG GTT GG | 45 | 0 | luc, | 100 |
| 215 TTT GCA ACC CC | 55 | .9091 | luc, | 101 |
| 143 ATC CTC CCA ACT TCG ACA TA | 45 | NC | Nonsense | 102 |
| 371 TGC CGA GCA CCG GCT TCA | 60 | NC | Nonsense | 103 |
| 373 TCC ACT TGC C | 60 | NC | Nonsense | 104 |
| 62-1 TTC TTC GAT AGT GCT CAT AC | 40 | NC | acpP | 105 |
| 62-2 TC TTC GAT AGT GCT CAT A | 39 | NC | acpP | 106 |
| 62-3 C TTC GAT AGT GCT CAT | 44 | NC | acpP | 107 |
| 62-4 TC GAT AGT GCT CAT | 43 | NC | acpP | 108 |
| 169 C TTC GAT AGT G | 45 | NC | acpP | 109 |
| 379 TTC GAT AGT G | 40 | NC | acpP | 110 |
| 380 TTC GAT AGT | 33 | NC | acpP | 111 |

TABLE 4-continued

PMO Sequences

| PMO | Sequence (5' to 3') | % GC | 2° Score | Target | SEQ ID NO |
|---|---|---|---|---|---|
| 381 | TC GAT AGT | 38 | NC | acpP | 112 |
| 382 | TC GAT AG | 43 | NC | acpP | 113 |
| 383 | C GAT AG | 50 | NC | acpP | 114 |
| 62-5 | TTG TCC TGA ATA TCA CTT CG | 40 | NC | Nonsense | 115 |
| 62-7 | G TCC TGA ATA TCA CTT | 38 | NC | Nonsense | 116 |
| 62-8 | TCG TGA GTA TCA CT | 43 | NC | Nonsense | 117 |
| 170 | TCT CAG ATG GT | 45 | NC | Nonsense | 118 |
| 384 | AAT CGG A | 43 | NC | Nonsense | 119 |
|  | ACG TTG AGG C | 60 | NC | luc | 120 |
|  | TCC ACT TGC C | 60 | NC | luc | 121 |
| 13 | TTC CAT TGG TTC AAA CAT AG | 35 | NC | FtsZ | 122 |
| 162 | C CAT TGG TTC | 50 | NC | FtsZ | 123 |
| 17 | CTC TCG CAA GGT CGC TCA | 60 | NC | GyrA | 124 |
| 164 | CTC TCG CAA GG | 70 | NC | GyrA | 125 |

EXAMPLE 1

Antisense Activity as a Function of Varying Length and Target Position

PMO (Table 4) of various length (from 7 to 20 bases) that are complementary to the region around the start codon of myc-luc mRNA were added to growing cultures of E. coli SM101 (pSE380myc-luc). One series of PMO was constructed by reducing the length at the 3' end (SEQ ID NOS: 59-71), and another by reducing the length at the 5' end (SEQ ID NOS:71-83). After 8 h in culture, luciferase was measured. Compared to a culture without PMO, 3' truncated PMO inhibited luciferase from 16 to 95% (FIG. 4, striped bars), and 5' truncated PMO inhibited luciferase from 6 to 89% (FIG. 4, solid bars). Results are discussed above.

PMO from the same two series were added individually to bacterial, cell-free protein synthesis reactions programmed to express myc-luciferase. These experiments were designed to eliminate the effects of entry of PMO into the cell, and to test the PMO at 37° C. instead of the permissive growth temperature (30° C.) of the conditional mutant SM101. PMO truncated at the 3' end from 10 to 20 bases in length inhibited about the same (FIG. 5, striped bars). The results are discussed above.

Figure 6:
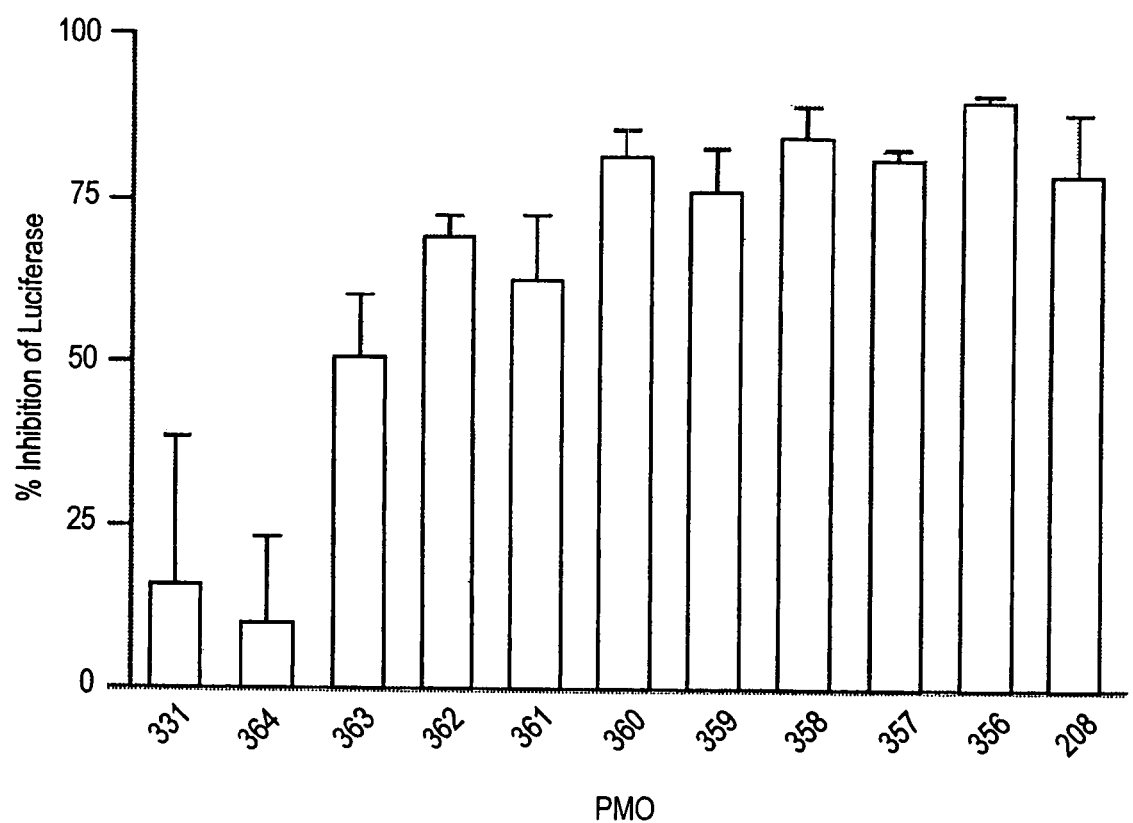
FIG. 6 shows the effect of antisense position near the start codon. Overlapping, isometric (10-base) PMO complementary to the region around the start codon of the myc-luc reporter gene, were added (100 nM) to bacterial, cell-free translation reactions programmed to make myc-luc. PMO identification number (Table 4) is shown under each bar.

A series of isometric (10-base) PMO, which varied by one base at each end (Table 4, SEQ ID NOS:91-99) and was targeted to the region around the AUG start condon of myc-luc, was added to bacterial, cell-free reactions programmed to synthesize myc-luc. All PMO inhibited luciferase expression (FIG. 6). A trend toward more inhibition was apparent as the target position moved downstream of the start codon. There was no correlation between inhibition and inclusion of the anti-start codon within the PMO sequence.

Figure 7:
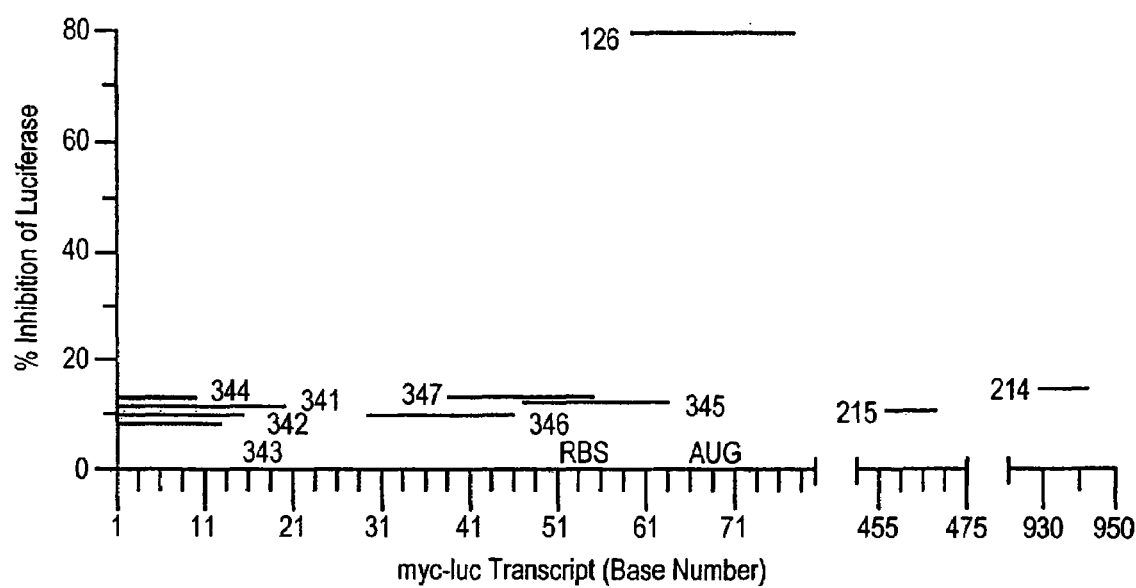
FIG. 7 shows the effect of antisense position upstream and downstream of the myc-luc start codon. PMO complementary to the various regions along the myc-luc transcript were added (200 nM) to bacterial, cell-free translation reactions programmed to make myc-luc. The lateral position of each PMO along the X axis indicates its complementary position on the myc-luc transcript. The vertical position of each PMO line indicates percent inhibition relative to a control reaction without PMO.

PMO of various lengths were targeted to various positions within the transcript of the myc-luc, including the extreme 5' end of the transcript (PMO 341-344, SEQ ID NOS:84-87), the ribosome binding site (PMO 345 and 347, SEQ ID NOS: 88 and 90), the region upstream of the ribosome binding site (PMO 346, SEQ ID NO:89), the region around and immediately downstream of the start codon (PMO 126, SEQ ID NO:71), and 3'coding region of luciferase (PMO 214 and 215, SEQ ID NOS:100 and 101). Each PMO was added to a bacterial cell-free protein synthesis reaction programmed with myc-luc mRNA, and luciferase light production was measured after 1 h at 37° C. The results show that only PMO 126 inhibited significantly (FIG. 7). Nonsense base sequence controls of 10 and 20 bases in length inhibited 4 and 6%, respectively.

Statistical analysis of all PMO targeted to myc-luc, or only the 10-base isometric series indicated no correlation ($r=-0.09785$, $P=0.5428$, and $r=-0.4572$, $P=0.1912$, respectively) between inhibition in the cell-free reactions and percent C+G content. However, an analysis of 37 myc PMO (FIG. 8A), excluding those shorter than 9 bases (327, 328, 333, and 334, SEQ ID NOS:60, 59, 82 and 83) and those in the 3' coding region of Luc (214 and 215), revealed a significant negative correlation ($r=-0.8497$, $P<0.0001$) between inhibition of reporter expression and 2° score of the PMO (Table 1). The 2° score is the fraction of bases in the PMO that are complementary to double stranded secondary structure within the folded target mRNA (Zuker 2003). An analysis of all 10-base PMO targeted to myc-luc also showed a significant negative correlation ($r=-0.9067$, $P=0.0003$) between inhibition and 2° score (FIG. 8B).

Previous work in eukaryotic systems suggests that PMO in the 13-14 subunit length are ineffective. We treated HeLa cell cultures that expressed myc-luc with 10 μM myc PMO of 2 lengths (11- and 20-bases, PMO 340 and 126, SEQ ID NOS: 63 and 71). Luciferase was measured at 7 and 24 hours after treatment. The results show that both PMO inhibited luciferase expression (FIG. 11). The 11 base PMO inhibited nearly as well as the 20 base PMO at 7 hours, but the longer PMO inhibited greater at 24 h. Non-specific inhibition was less at both times, as indicated by the culture treated with nonsense PMO 143 (SEQ ID NO:102).

The 3' truncated series of myc PMO were tested for inhibition of luciferase in a cell-free protein translation reaction made with eukaryotic (rabbit reticulocyte) components. The 20 base PMO inhibited significantly more than the shorter PMO (FIG. 12). There was a sharp decrease in inhibition between the 20 base and 18 base PMO. There was a trend of inhibition that generally favored the longer PMO.

EXAMPLE 2

Acyl Carrier Protein as an Endogenous Bacterial Gene Target

The effect of PMO was tested on an endogenous bacterial gene that encodes acyl carrier protein, acpP, which is essential for viability (Zhang and Cronan 1996) and has been used previously to inhibit bacterial growth (Good, Awasthi et al. 2001; Geller, Deere et al. 2003). PMO from 6 to 20 bases in length and complementary to region around the start codon in mRNA for acpP (Table 3, SEQ ID NOS:105-114) were added to growing cultures of AS19 and growth at 37 C was monitored by optical density and viable cell counts. Growth curves were normal for all cultures except for that with the 11 base PMO, which caused significant inhibition (FIG. 9A). Slight and reproducible, but statistically insignificant inhibitions of OD occurred in cultures with the 10 and 14 base PMO. Viable cells were significantly reduced in 8 h cultures that contained PMO of 10, 11 or 14 bases (FIG. 9B). No reduction in CFU was apparent in cultures treated with PMO of less than 10 or more than 14 bases in length. Cultures without PMO, or with a nonsense base sequence did not inhibit growth.

PMO of various lengths (from 6 to 20 bases) and targeted to acpP were added to bacterial, cell-free protein synthesis reactions programmed to express an acpP-luc reporter. The results (FIG. 10) show that PMO 11 to 20 bases in length inhibited reporter expression to about the same extent. PMO shorter than 11 bases in length, or nonsense sequence controls did not inhibit significantly.

The above results with acpP and nonsense PMOs suggest that inhibition was sequence specific. To demonstrate directly a sequence-specific effect, mice were infected with *E. coli* AS19 that expresses firefly luciferase, then treated at 0 and 13 h post-infection with a PMO (luc) complementary to the region around the start codon of the luciferase transcript, or a nonsense PMO. Peritoneal lavages were collected at 13 and 22 h post-infection and analyzed for CFU, luciferase activity, and luciferase and OmpA protein (western immuno-blot). As expected, the results show no inhibition of growth with luc PMO treatment compared to nonsense PMO treatment (Table 4). Luciferase activity in samples from luc PMO-treated mice was inhibited 53% and 46% at 13 and 22 h, respectively, compared to samples from nonsense PMO-treated mice (Table 4).

Western blot analysis agreed closely with the results of luciferase activity. In samples from luc PMO-treated mice, there was a 68% and 47% reduction in the amount of luciferase protein at 13 and 22 h, respectively, compared to samples from nonsense PMO-treated mice (Table 2).

TABLE 4

Gene Specific Inhibition

| | | | Luciferase Activity | | | Western Blot | | |
|---|---|---|---|---|---|---|---|---|
| PMO Treatment | Time after treatment (h) | CFU/ml ($\times 10^6$) | RLU/CFU Mean (SEM) n = 8 | P | % Inhibition | Luc/OmpA Mean (SEM) n = 7-8 | P | % Inhibition |
| Luc | 13 | 6.3 | 2.90 (0.629) | .0035 | 53 | 0.122 (.0312) | .0002 | 68 |
| Nonsense | 13 | 4.3 | 6.19 (0.773) | | 0 | 0.382 (.0296) | | 0 |
| Luc | 22 | 0.96 | 3.20 (0.582) | .0093 | 46 | 0.147 (.0363) | .0145 | 57 |
| Nonsense | 22 | 0.39 | 8.12* (1.94) | | 0 | 0.339 (.0668) | | 0 |

EXAMPLE 3

In vivo Antisense Antibacterial Activity

Groups of 4 mice were injected IP with *E. coli* AS19, which has a genetic defect that makes it abnormally permeable to high MW solutes. Immediately following infection, each mouse was injected IP with 300 μg of an 11-base PMO complementary to acpP, an 11-base nonsense sequence PMO, or PBS.

Peritoneal lavages were collected at 2, 7, 13, and 23 h post-infection, and plated for bacteria. The results show that at all times analyzed, the acpP PMO-treated mice had significantly (P<0.05) lower CFU than the mice treated with either nonsense PMO or PBS (FIG. 13). The differences between the acpP PMO-treated group and the nonsense PMO control ranges from 39-fold at 2 h to 600-fold at 23 h.

The same PMOs were again tested, except with *E. coli* SM105, which has a normal outer membrane. AcpP PMO reduced CFU by 84% compared to nonsense PMO at 12 h post-infection. There was no reduction of CFU at 2, 6, or 24 h (FIG. 14). Mice were injected with a second dose at 24 h post-infection. By 48 h post-infection the CFU of acpP PMO-treated mice were 70% lower than the CFU of nonsense PMO-treated mice (FIG. 14).

EXAMPLE 4

Figure 16:
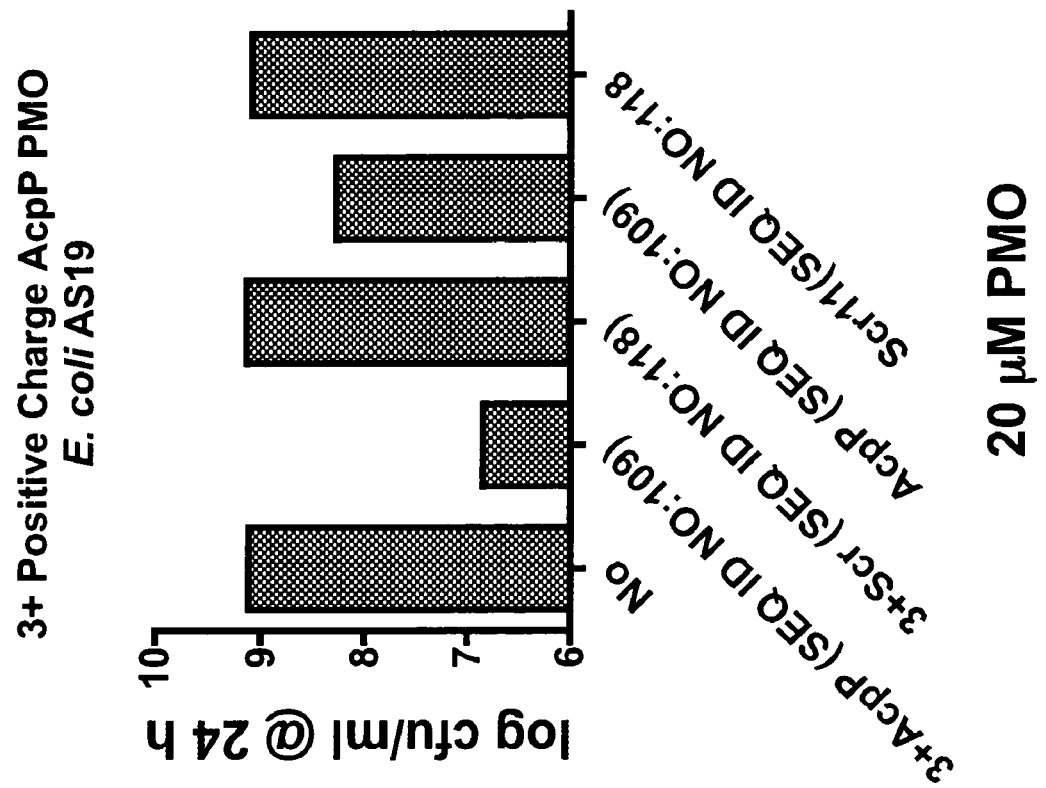
FIG. 16 shows the CFU/ml of E. coli AS19 cultures after treatment with a +PMO version of acpP containing three cationic linkages compared to the uncharged acpP PMO.

Enhanced in vitro Antisense Antibacterial Activity Using PMO with Positive Charged Linkages Two PMOs with cationic linkages ((1 piperazino) phosphinylideneoxy linkages, see above) interspersed throughout the sequences were synthesized and used to treat cultures of *E. coli* strain AS19. The positively charged PMOs were modifications of the AcpP11 PMO and its scramble control, acpP-scr (SEQ ID NOS: 109 and 118, respectively). The location of the three positive charges in the PMO are as follows: acpP (5'-C+TT CGA+TAG+TG); AcpP-scr (5'-TC+T CAG A+TG G+T). An overnight culture of AS19 was diluted to $5\times10^5$ cells/ml in Mueller-Hinton broth and PMO were added to a final concentration of 20 micromolar. Growth was allowed for 24 hours at 37 degrees C. before viable cells were determined by plating on LB agar plates. FIG. 16 shows a graph of the viable cell count after treatment with the cationic PMO compared to their uncharged counterparts. An approximate 50 fold increase in antibacterial activity was observed using the acpP PMO with three positive charges as compared to the uncharged acpP PMO.

| Name | Sequence (5' to 3') | SEQ ID NO |
|---|---|---|
| *E. coli* ftsZ | GAGAGAAACTATGTTTGAACCAATGGAACTT | 1 |
| *E. coli* acpP | ATTTAAGAGTATGAGCACTATCGAAGAACGC | 2 |
| *E. coli* gyrA | TAGCGGTTAGATGAGCGACCTTGCGAGAGAA | 3 |
| *E. coli* O157:H7 ftsZ | GAGAGAAACTATGTTTGAACCAATGGAACTT | 4 |
| *E. coli* O157:H7 acpP | ATTTAAGAGTATGAGCACTATCGAAGAACGC | 5 |
| *E. coli* O157:H7 gyrA | TAGCGGTTAGATGAGCGACCTTGCGAGAGAA | 6 |
| *S. typhimurium* ftsZ | GAGAGAGATTATGTTTGAACCTATGGAACTA | 7 |
| *S. typhimurium* acpP | ATTTAAGAGTATGAGCACTATCGAAGAACGC | 8 |
| *S. typhimurium* gyrA | TAGCGGTTAGATGAGCGACCTTGCGAGAGAA | 9 |
| *S. aeruginosa* ftsZ | GAGAGGGGAAATGTTTGAACTGGTCGATAAC | 10 |
| *S. aeruginosa* acpP | AAAACAAGGTATGAGCACCATCGAAGAACGC | 11 |
| *S. aeruginosa* gyrA | CAGGCTTCTCATGGGCGAACTGGCCAAAGAA | 12 |
| *V. cholera* ftsZ | GAGATAACACATGTTTGAACCGATGATGGAA | 13 |
| *V. cholera* acpP | ACTATATTGGATGGTTTATATGTCTATCTCT | 14 |
| *V. cholera* gyrA | TAATGGCTCTATGAGCGATCTAGCTAAAGAG | 15 |
| *N. gonorrhoea* ftsZ | GAGTTTTTGAATGGAATTTGTTTACGACGT | 16 |
| *N. gonorrhoea* acpP | AACGACTGATATGTCAAACATCGAACAACA | 17 |
| *N. gonorrhoea* gyrA | CATTGAAACCATGACCGACGCAACCATCCG | 18 |
| *S. aureus* ftsZ | GGAAATTTAAATGTTAGAATTTGAACAAGGA | 19 |
| *S. aureus* gyrA | GGAACTCTTGATGGCTGAATTACCTCAATCA | 20 |
| *S. aureus* fmhB | ATCATAAATCATGGAAAAGATGCATATCAC | 21 |
| *M. tuberculosis* ftsZ | CTCTAAGCCTATGGTTGAGGTTGAGAGTTTG | 22 |
| *M. tuberculosis* acpP | CCCGGGCGCGATGTGGCGATATCCACTAAGT | 23 |
| *M. tuberculosis* gyrA | CGAGGAATAGATGACAGACACGACGTTGCCG | 24 |
| *M. tuberculosis* pimA | GGAAAGCCTGATGCGGATCGGCATGATTTG | 25 |
| *M. tuberculosis* cysS2 | CTGGCACGTCGTGACCGATCGGGCTCGCTT | 26 |
| *H. pylori* ftsZ | GAATGTGGCTATGGTTCATCAATCAGAGATG | 27 |
| *H. pylori* acpP | AGTTTTAATTATGGCTTTATTTGAAGATATT | 28 |
| *H. pylori* gyrA | AGGGAGACACATGCAAGATAATTCAGTCAAT | 29 |
| *S. pneumoniae* ftsZ | AAAATAAATTATGACATTTTCATTTGATACA | 30 |
| *S. pneumoniae* acpP | GAGTCCTATCATGGCAGTATTTGAAAAAGTA | 31 |
| *S. pneumoniae* gyrA | GCATTTATTAATGCAGGATAAAAATTTAGTG | 32 |
| *T. palladium* ftsZ | TGGGAGGGGAATGATGAATATAGAGCTTGCA | 33 |
| *T. palladium* acpP | TGCCCCGTGGATGAGTTGTTCTTAAGAATGA | 34 |
| *T. palladium* gyrA | TGCCCGCCCTATGGAAGAAATTAGCACCCCA | 35 |
| *C. trachomatis* acpP | GGATCATAGGATGAGTTTAGAAGATGATGTA | 36 |
| *C. trachomatis* gyrA | AAACGAACTTATGAGCGACCTCTCGGACCTA | 37 |
| *B. henselae* ftsZ | AGGCAAATTAATTGGTAAAAAATTAGAGAG | 38 |
| *B. henselae* acpP | GGATTTCAACATGAGTGATACAGTAGAGCG | 39 |
| *B. henselae* gyrA | GTCTAAAGCTGTGACAGATCTAAACCCGCA | 40 |
| *H. influenzae* ftsZ | GAGAACATCAATGCTATACCCAGAGTACCCT | 41 |
| *H. influenzae* acpP | GGAAAAACAAATGAGTATTGAAGAACGCGTG | 42 |
| *H. influenzae* gyrA | AGGAATACCAATGACGGATTCAATCCAATCA | 43 |
| *Y. pestis* ftsZ | GAGAGAAACTATGTTTGAACCTATGGAACT | 44 |
| *Y. pestis* acpP | ATTTAAGAGTATGAGCACTATCGAAGAACG | 45 |
| *Y. pestis* gyrA | TAGCGGCTCAATGAGCGACCTTGCCAGAGA | 46 |
| *B. anthracis* ftsZ | GGATTTCGACATGTTAGAGTTTGATACTAC | 47 |
| *B. anthracis* acpP | GGTGAATGGAATGGCAGATGTTTTAGAGCG | 48 |
| *B. anthracis* gyrA | GTGCTCGTTGATGTCAGACAATCAACAACA | 49 |
| *B. mellei* ftsZ | GGAGGCAACAATGGAATTCGAAATGCTGGA | 50 |
| *B. mallei* acpP | CGGAGGGGTAATGGACAACATCGAACAACG | 51 |
| *B. mallei* gyrA | ATACGGATACATGGATCAATTCGCCAAAGA | 52 |
| *B. pseudomallei* ftsZ | GGAGGCAACAATGGAATTCGAAATGCTGGA | 53 |
| *B. pseudomallei* acpP | CGGAGGGGTAATGGACAACATCGAACAACG | 54 |
| *B. pseudomallei* gyrA | ATACGGATACATGGATCAATTCGCCAAAGA | 55 |
| *F. tularensis* ftsZ | GGAGTAAAATATGTTTGATTTTAACGATTC | 56 |
| *F. tularensis* acpP | AGGAAAAAATATGAGTACACATAACGAAGA | 57 |
| *F. tularensis* gyrA | GCGATAACTAATGTCTATAATTACTAAAGA | 58 |
| 328 | ACGTTGA | 59 |
| 327 | ACGTTGAG | 60 |
| 326 | ACGTTGAGG | 61 |
| 208 | ACGTTGAGGG | 62 |
| 340 | ACGTTGAGGGG | 63 |
| 298 | ACGTTGAGGGGC | 64 |
| 250 | ACGTTGAGGGGCA | 65 |
| 249 | ACGTTGAGGGGCAT | 66 |
| 248 | ACGTTGAGGGGCATC | 67 |
| 247 | ACGTTGAGGGGCATCG | 68 |
| 246 | ACGTTGAGGGGCATCGT | 69 |
| 245 | ACGTTGAGGGGCATCGTC | 70 |
| 126 | ACGTTGAGGGGCATCGTCGC | 71 |
| 239 | GTTGAGGGGCATCGTCGC | 72 |
| 240 | TTGAGGGGCATCGTCGC | 73 |
| 241 | TGAGGGGCATCGTCGC | 74 |
| 242 | GAGGGGCATCGTCGC | 75 |
| 243 | AGGGGCATCGTCGC | 76 |
| 244 | GGGGCATCGTCGC | 77 |

-continued

| Name | Sequence (5' to 3') | SEQ ID NO |
|---|---|---|
| 329 | GGGCATCGTCGC | 78 |
| 330 | GGCATCGTCGC | 79 |
| 331 | GCATCGTCGC | 80 |
| 332 | CATCGTCGC | 81 |
| 333 | ATCGTCGC | 82 |
| 334 | TCGTCGC | 83 |
| 341 | GGAAACCGTTGTGGTCTCCC | 84 |
| 342 | ACCGTTGTGGTCTCCC | 85 |
| 343 | GTTGTGGTCTCCC | 86 |
| 344 | GTGGTCTCCC | 87 |
| 345 | CGTCGCGGGATTCCTTCT | 88 |
| 346 | AAAGTTAAACAAAATTAT | 89 |
| 347 | TCCTTCTTAAAGTTAAAC | 90 |
| 356 | CGTTGAGGGG | 91 |
| 357 | GTTGAGGGGC | 92 |
| 358 | TTGAGGGGCA | 93 |
| 359 | TGAGGGGCAT | 94 |
| 360 | GAGGGGCATC | 95 |
| 361 | AGGGGCATCG | 96 |
| 362 | GGGGCATCGT | 97 |
| 363 | GGGCATCGTC | 98 |
| 364 | GGCATCGTCG | 99 |
| 214 | AATAGGGTTGG | 100 |
| 215 | TTTGCAACCCC | 101 |
| 143 | ATCCTCCCAACTTCGACATA | 102 |
| 371 | TGCCGAGCACCGGCTTCATA | 103 |
| 373 | TCCACTTGCC | 104 |
| 62-1 | TTCTTCGATAGTGCTCATAC | 105 |
| 62-2 | TCTTCGATAGTGCTCATA | 106 |
| 62-3 | CTTCGATAGTGCTCAT | 107 |
| 62-4 | TCGATAGTGCTCAT | 108 |
| 169 | CTTCGATAGTG | 109 |
| 379 | TTCGATAGTG | 110 |
| 380 | TTCGATAGT | 111 |
| 381 | TCGATAGT | 112 |
| 382 | TCGATAG | 113 |
| 383 | CGATAG | 114 |
| 62-5 | TTGTCCTGAATATCACTTCG | 115 |
| 62-7 | GTCCTGAATATCACTT | 116 |
| 62-8 | TCGTGAGTATCACT | 117 |
| 170 | TCTCAGATGGT | 118 |
| 384 | AATCGGA | 119 |
|  | ACGTTGAGG C | 120 |
|  | TCCACTTGC C | 121 |
| 13 | TTCCATTGGTTCAAACATAG | 122 |
| 162 | CCATTGGTTC | 123 |
| 17 | CTCTCGCAAGGTCGCTCATC | 124 |
| 164 | CTCTCGCAAGG | 125 |
| E. coli acpP | TGCTCATACTC | 126 |
| E. coli acpP | ATAGTGCTCAT | 127 |
| E. coli acpP | GCGTTCTTCCG | 128 |

It is claimed:

1. A method of inhibiting the growth of *Escherichia coli*, *Salmonella typhimurium*, or *Yersinia pestis* pathogenic bacterial cells, comprising exposing the bacterial cells to a growth-inhibiting amount of an antisense oligonucleotide compound, composed of morpholino subunits and phosphorus-containing intersubunit linkages joining a morpholino nitrogen of one subunit to a 5' exocyclic carbon of an adjacent subunit, and having:

(i) no more than 12 nucleotide bases,
   (ii) a targeting nucleic acid sequence of no fewer than 10 bases in length that is complementary to a target sequence containing or within 10 bases, in a downstream direction, of the translational start codon in SEQ ID NO: 2; and
   (iii) a $T_m$, when hybridized with the target sequence, between 50° to 60° C.;

wherein said morpholino subunits in the oligonucleotide compound are joined by a combination of (a) uncharged phosphorodiamidate linkages, in accordance with structure I,

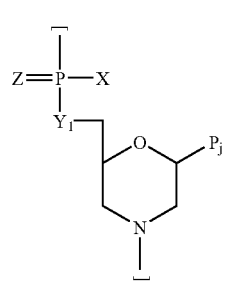

where $Y_1$=O, Z=O, Pj is a purine or pyrimidine base-pairing moiety effective to bind, by base-specific hydrogen bonding, to a base in a polynucleotide, and X is amino or alkyl amino, including dialkylamino; and (b) cationic phosphorodiamidate linkages in accordance with structure I, where $Y_1$=O, Z=O, and $P_j$ are as defined above, and X is 1-piperazino;

and wherein said cationic linkages make up no more than about half the total number of linkages.

2. The method of claim 1, wherein X in said uncharged linkages is $N(CH_3)_2$.

3. The method of claim 1, wherein the oligonucleotide compound to which the cells are exposed has a targeting sequence that is complementary to a target sequence containing the translational start codon of the bacterial mRNA.

4. The method of claim 1, wherein the oligonucleotide compound to which the cells are exposed has a targeting sequence that is complementary to a target sequence that is within 10 bases, in a downstream direction, of the translational start codon of the bacterial mRNA.

5. The method of claim 1, wherein the oligonucleotide compound to which the cells are exposed contains only 11 bases, and its nucleic acid sequence is completely complementary to the mRNA target sequence.

6. The method of claim 1, for use in inhibiting a bacterial *Escherichia coli, Salmonella typhimurium*, or *Yersinia pestis* infection in a mammalian subject, wherein said exposing includes administering said compound in a therapeutically effective amount.

* * * * *

UNITED STATES PATENT AND TRADEMARK OFFICE
CERTIFICATE OF CORRECTION

PATENT NO. : 7,625,873 B2  Page 1 of 1
APPLICATION NO. : 11/432216
DATED : December 1, 2009
INVENTOR(S) : Geller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 311 days.

Signed and Sealed this

Second Day of November, 2010

David J. Kappos
*Director of the United States Patent and Trademark Office*

SEQUENCE LISTING

<160> NUMBER OF SEQ ID NOS: 128

<210> SEQ ID NO 1
<211> LENGTH: 31
<212> TYPE: DNA
<213> ORGANISM: Escherichia coli

<400> SEQUENCE: 1
gagagaaact atgtttgaac caatggaact t         31

<210> SEQ ID NO 2
<211> LENGTH: 31
<212> TYPE: DNA
<213> ORGANISM: Escherichia coli -continued

```
<400> SEQUENCE: 2
atttaagagt atgagcacta tcgaagaacg c                                    31

<210> SEQ ID NO 3
<211> LENGTH: 31
<212> TYPE: DNA
<213> ORGANISM: Escherichia coli

<400> SEQUENCE: 3
tagcggttag atgagcgacc ttgcgagaga a                                    31

<210> SEQ ID NO 4
<211> LENGTH: 31
<212> TYPE: DNA
<213> ORGANISM: Escherichia coli

<400> SEQUENCE: 4
gagagaaact atgtttgaac caatggaact t                                    31

<210> SEQ ID NO 5
<211> LENGTH: 31
<212> TYPE: DNA
<213> ORGANISM: Escherichia coli

<400> SEQUENCE: 5
atttaagagt atgagcacta tcgaagaacg c                                    31

<210> SEQ ID NO 6
<211> LENGTH: 31
<212> TYPE: DNA
<213> ORGANISM: Escherichia coli

<400> SEQUENCE: 6
tagcggttag atgagcgacc ttgcgagaga a                                    31

<210> SEQ ID NO 7
<211> LENGTH: 31
<212> TYPE: DNA
<213> ORGANISM: Salmonella typhimurium

<400> SEQUENCE: 7
gagagagatt atgtttgaac ctatggaact a                                    31

<210> SEQ ID NO 8
<211> LENGTH: 31
<212> TYPE: DNA
<213> ORGANISM: Salmonella typhimurium

<400> SEQUENCE: 8
atttaagagt atgagcacta tcgaagaacg c                                    31

<210> SEQ ID NO 9
<211> LENGTH: 31
<212> TYPE: DNA
<213> ORGANISM: Salmonella typhimurium

<400> SEQUENCE: 9
tagcggttag atgagcgacc ttgcgagaga a                                    31

<210> SEQ ID NO 10
<211> LENGTH: 31
<212> TYPE: DNA
<213> ORGANISM: Pseudomonas aeruginosa
```

```
<400> SEQUENCE: 10 gagagggaa atgtttgaac tggtcgataa c                              31

<210> SEQ ID NO 11
<211> LENGTH: 31
<212> TYPE: DNA
<213> ORGANISM: Pseudomonas aeruginosa

<400> SEQUENCE: 11
aaaacaaggt atgagcacca tcgaagaacg c                             31

<210> SEQ ID NO 12
<211> LENGTH: 31
<212> TYPE: DNA
<213> ORGANISM: Pseudomonas aeruginosa

<400> SEQUENCE: 12
caggcttctc atgggcgaac tggccaaaga a                             31

<210> SEQ ID NO 13
<211> LENGTH: 31
<212> TYPE: DNA
<213> ORGANISM: Vibrio cholera

<400> SEQUENCE: 13
gagataacac atgtttgaac cgatgatgga a                             31

<210> SEQ ID NO 14
<211> LENGTH: 31
<212> TYPE: DNA
<213> ORGANISM: Vibrio cholera

<400> SEQUENCE: 14
actatattgg atggtttata tgtctatctc t                             31

<210> SEQ ID NO 15
<211> LENGTH: 31
<212> TYPE: DNA
<213> ORGANISM: Vibrio cholera

<400> SEQUENCE: 15
taatggctct atgagcgatc tagctaaaga g                             31

<210> SEQ ID NO 16
<211> LENGTH: 30
<212> TYPE: DNA
<213> ORGANISM: Neisseria gonorrhoea

<400> SEQUENCE: 16 gagttttga atggaatttg tttacgacgt                                30

<210> SEQ ID NO 17
<211> LENGTH: 30
<212> TYPE: DNA
<213> ORGANISM: Neisseria gonorrhoea

<400> SEQUENCE: 17
aacgactgat atgtcaaaca tcgaacaaca                               30

<210> SEQ ID NO 18
<211> LENGTH: 30
<212> TYPE: DNA
```

<213> ORGANISM: Neisseria gonorrhoea

<400> SEQUENCE: 18
cattgaaacc atgaccgacg caaccatccg                               30

<210> SEQ ID NO 19
<211> LENGTH: 31
<212> TYPE: DNA
<213> ORGANISM: Staphylococcus aureus

<400> SEQUENCE: 19
ggaaatttaa atgttagaat ttgaacaagg a                             31

<210> SEQ ID NO 20
<211> LENGTH: 31
<212> TYPE: DNA
<213> ORGANISM: Staphylococcus aureus

<400> SEQUENCE: 20
ggaactcttg atggctgaat tacctcaatc a                             31

<210> SEQ ID NO 21
<211> LENGTH: 30
<212> TYPE: DNA
<213> ORGANISM: Staphylococcus aureus

<400> SEQUENCE: 21
atcataaatc atggaaaaga tgcatatcac                               30

<210> SEQ ID NO 22
<211> LENGTH: 31
<212> TYPE: DNA
<213> ORGANISM: Mycobacterium tuberculosis

<400> SEQUENCE: 22
ctctaagcct atggttgagg ttgagagttt g                             31

<210> SEQ ID NO 23
<211> LENGTH: 31
<212> TYPE: DNA
<213> ORGANISM: Mycobacterium tuberculosis

<400> SEQUENCE: 23
cccgggcgcg atgtggcgat atccactaag t                             31

<210> SEQ ID NO 24
<211> LENGTH: 31
<212> TYPE: DNA
<213> ORGANISM: Mycobacterium tuberculosis

<400> SEQUENCE: 24
cgaggaatag atgacagaca cgacgttgcc g                             31

<210> SEQ ID NO 25
<211> LENGTH: 30
<212> TYPE: DNA
<213> ORGANISM: Mycobacterium tuberculosis

<400> SEQUENCE: 25
ggaaagcctg atgcggatcg gcatgatttg                               30

<210> SEQ ID NO 26
<211> LENGTH: 30

-continued

```
<212> TYPE: DNA
<213> ORGANISM: Mycobacterium tuberculosis

<400> SEQUENCE: 26
ctggcacgtc gtgaccgatc gggctcgctt                                    30

<210> SEQ ID NO 27
<211> LENGTH: 31
<212> TYPE: DNA
<213> ORGANISM: Helicobacter pylori

<400> SEQUENCE: 27
gaatgtggct atggttcatc aatcagagat g                                  31

<210> SEQ ID NO 28
<211> LENGTH: 31
<212> TYPE: DNA
<213> ORGANISM: Helicobacter pylori

<400> SEQUENCE: 28
agttttaatt atggctttat ttgaagatat t                                  31

<210> SEQ ID NO 29
<211> LENGTH: 31
<212> TYPE: DNA
<213> ORGANISM: Helicobacter pylori

<400> SEQUENCE: 29
agggagacac atgcaagata attcagtcaa t                                  31

<210> SEQ ID NO 30
<211> LENGTH: 31
<212> TYPE: DNA
<213> ORGANISM: Streptococcus pneumoniae

<400> SEQUENCE: 30
aaaataaatt atgacatttt catttgatac a                                  31

<210> SEQ ID NO 31
<211> LENGTH: 31
<212> TYPE: DNA
<213> ORGANISM: Streptococcus pneumoniae

<400> SEQUENCE: 31
gagtcctatc atggcagtat ttgaaaaagt a                                  31

<210> SEQ ID NO 32
<211> LENGTH: 31
<212> TYPE: DNA
<213> ORGANISM: Streptococcus pneumoniae

<400> SEQUENCE: 32
gcatttatta atgcaggata aaaatttagt g                                  31

<210> SEQ ID NO 33
<211> LENGTH: 31
<212> TYPE: DNA
<213> ORGANISM: Treponema palladium

<400> SEQUENCE: 33
tgggagggga atgatgaata tagagcttgc a                                  31

<210> SEQ ID NO 34
```

```
<210> SEQ ID NO 34
<211> LENGTH: 31
<212> TYPE: DNA
<213> ORGANISM: Treponema palladium

<400> SEQUENCE: 34
tgccccgtgg atgagttgtt cttaagaatg a                                31

<210> SEQ ID NO 35
<211> LENGTH: 31
<212> TYPE: DNA
<213> ORGANISM: Treponema palladium

<400> SEQUENCE: 35
tgcccgccct atggaagaaa ttagcacccc a                                31

<210> SEQ ID NO 36
<211> LENGTH: 31
<212> TYPE: DNA
<213> ORGANISM: Chlamydia trachomatis

<400> SEQUENCE: 36
ggatcatagg atgagtttag aagatgatgt a                                31

<210> SEQ ID NO 37
<211> LENGTH: 31
<212> TYPE: DNA
<213> ORGANISM: Chlamydia trachomatis

<400> SEQUENCE: 37
aaacgaactt atgagcgacc tctcggacct a                                31

<210> SEQ ID NO 38
<211> LENGTH: 30
<212> TYPE: DNA
<213> ORGANISM: Bartonella henselae

<400> SEQUENCE: 38
aggcaaatta attggtaaaa aattagagag                                  30

<210> SEQ ID NO 39
<211> LENGTH: 30
<212> TYPE: DNA
<213> ORGANISM: Bartonella henselae

<400> SEQUENCE: 39
ggatttcaac atgagtgata cagtagagcg                                  30

<210> SEQ ID NO 40
<211> LENGTH: 30
<212> TYPE: DNA
<213> ORGANISM: Bartonella henselae

<400> SEQUENCE: 40
gtctaaagct gtgacagatc taaacccgca                                  30

<210> SEQ ID NO 41
<211> LENGTH: 31
<212> TYPE: DNA
<213> ORGANISM: Haemophilus influenzae

<400> SEQUENCE: 41
gagaacatca atgctatacc cagagtaccc t                                31
```

<210> SEQ ID NO 42
<211> LENGTH: 31
<212> TYPE: DNA
<213> ORGANISM: Haemophilus influenzae

<400> SEQUENCE: 42
ggaaaaacaa atgagtattg aagaacgcgt g                          31

<210> SEQ ID NO 43
<211> LENGTH: 31
<212> TYPE: DNA
<213> ORGANISM: Haemophilus influenzae

<400> SEQUENCE: 43
aggaatacca atgacggatt caatccaatc a                          31

<210> SEQ ID NO 44
<211> LENGTH: 30
<212> TYPE: DNA
<213> ORGANISM: Yersinia pestis

<400> SEQUENCE: 44
gagagaaact atgtttgaac ctatggaact                            30

<210> SEQ ID NO 45
<211> LENGTH: 30
<212> TYPE: DNA
<213> ORGANISM: Yersinia pestis

<400> SEQUENCE: 45
atttaagagt atgagcacta tcgaagaacg                            30

<210> SEQ ID NO 46
<211> LENGTH: 30
<212> TYPE: DNA
<213> ORGANISM: Yersinia pestis

<400> SEQUENCE: 46
tagcggctca atgagcgacc ttgccagaga                            30

<210> SEQ ID NO 47
<211> LENGTH: 30
<212> TYPE: DNA
<213> ORGANISM: Bacillus anthracis

<400> SEQUENCE: 47
ggatttcgac atgttagagt ttgatactac 30

<210> SEQ ID NO 48
<211> LENGTH: 30
<212> TYPE: DNA
<213> ORGANISM: Bacillus anthracis

<400> SEQUENCE: 48
ggtgaatgga atggcagatg ttttagagcg 30

<210> SEQ ID NO 49
<211> LENGTH: 30
<212> TYPE: DNA
<213> ORGANISM: Bacillus anthracis

<400> SEQUENCE: 49
gtgctcgttg atgtcagaca atcaacaaca 30

<210> SEQ ID NO 50
<211> LENGTH: 30
<212> TYPE: DNA
<213> ORGANISM: Burkholderia mallei

<400> SEQUENCE: 50
ggaggcaaca atggaattcg aaatgctgga                                    30

<210> SEQ ID NO 51
<211> LENGTH: 30
<212> TYPE: DNA
<213> ORGANISM: Burkholderia mallei

<400> SEQUENCE: 51
cggaggggta atggacaaca tcgaacaacg                                    30

<210> SEQ ID NO 52
<211> LENGTH: 30
<212> TYPE: DNA
<213> ORGANISM: Burkholderia mallei

<400> SEQUENCE: 52
atacggatac atggatcaat tcgccaaaga                                    30

<210> SEQ ID NO 53
<211> LENGTH: 30
<212> TYPE: DNA
<213> ORGANISM: Burkholderia pseudomallei

<400> SEQUENCE: 53
ggaggcaaca atggaattcg aaatgctgga                                    30

<210> SEQ ID NO 54
<211> LENGTH: 30
<212> TYPE: DNA
<213> ORGANISM: Burkholderia pseudomallei

<400> SEQUENCE: 54
cggaggggta atggacaaca tcgaacaacg                                    30

<210> SEQ ID NO 55
<211> LENGTH: 30
<212> TYPE: DNA
<213> ORGANISM: Burkholderia pseudomallei

<400> SEQUENCE: 55
atacggatac atggatcaat tcgccaaaga                                    30

<210> SEQ ID NO 56
<211> LENGTH: 30
<212> TYPE: DNA
<213> ORGANISM: Francisella tularensis

<400> SEQUENCE: 56
ggagtaaaat atgtttgatt ttaacgattc                                    30

<210> SEQ ID NO 57
<211> LENGTH: 30
<212> TYPE: DNA
<213> ORGANISM: Francisella tularensis

<400> SEQUENCE: 57
aggaaaaaat atgagtacac ataacgaaga                                    30

<210> SEQ ID NO 58
<211> LENGTH: 30
<212> TYPE: DNA
<213> ORGANISM: Francisella tularensis

<400> SEQUENCE: 58
gcgataacta atgtctataa ttactaaaga                                    30

<210> SEQ ID NO 59
<211> LENGTH: 7
<212> TYPE: DNA
<213> ORGANISM: Artificial Sequence
<220> FEATURE:
<223> OTHER INFORMATION: Synthetic oligomer

<400> SEQUENCE: 59 acgttga                                                              7

<210> SEQ ID NO 60
<211> LENGTH: 8
<212> TYPE: DNA
<213> ORGANISM: Artificial Sequence
<220> FEATURE:
<223> OTHER INFORMATION: Synthetic oligomer

<400> SEQUENCE: 60 acgttgag                                                             8

<210> SEQ ID NO 61
<211> LENGTH: 9
<212> TYPE: DNA
<213> ORGANISM: Artificial Sequence
<220> FEATURE:
<223> OTHER INFORMATION: Synthetic oligomer

<400> SEQUENCE: 61 acgttgagg                                                            9

<210> SEQ ID NO 62
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 62
acgttgaggg                                                          10

<210> SEQ ID NO 63
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 63
acgttgaggg g                                                        11

<210> SEQ ID NO 64
<211> LENGTH: 12
<212> TYPE: DNA
<213> ORGANISM: Artificial Sequence
<220> FEATURE:
<223> OTHER INFORMATION: Synthetic oligomer

```
<400> SEQUENCE: 64
acgttgaggg gc                                                    12

<210> SEQ ID NO 65
<211> LENGTH: 13
<212> TYPE: DNA
<213> ORGANISM: Artificial Sequence
<220> FEATURE:
<223> OTHER INFORMATION: Synthetic oligomer

<400> SEQUENCE: 65
acgttgaggg gca                                                   13

<210> SEQ ID NO 66
<211> LENGTH: 14
<212> TYPE: DNA
<213> ORGANISM: Artificial Sequence
<220> FEATURE:
<223> OTHER INFORMATION: Synthetic oligomer

<400> SEQUENCE: 66
acgttgaggg gcat                                                  14

<210> SEQ ID NO 67
<211> LENGTH: 15
<212> TYPE: DNA
<213> ORGANISM: Artificial Sequence
<220> FEATURE:
<223> OTHER INFORMATION: Synthetic oligomer

<400> SEQUENCE: 67
acgttgaggg gcatc                                                 15

<210> SEQ ID NO 68
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 68
acgttgaggg gcatcg                                                16

<210> SEQ ID NO 69
<211> LENGTH: 17
<212> TYPE: DNA
<213> ORGANISM: Artificial Sequence
<220> FEATURE:
<223> OTHER INFORMATION: Synthetic oligomer

<400> SEQUENCE: 69
acgttgaggg gcatcgt                                               17

<210> SEQ ID NO 70
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 70
acgttgaggg gcatcgtc                                              18

<210> SEQ ID NO 71
<211> LENGTH: 20
```

```
<212> TYPE: DNA
<213> ORGANISM: Artificial Sequence
<220> FEATURE:
<223> OTHER INFORMATION: Synthetic oligomer

<400> SEQUENCE: 71
acgttgaggg gcatcgtcgc                                              20

<210> SEQ ID NO 72
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 72
gttgaggggc atcgtcgc                                                18

<210> SEQ ID NO 73
<211> LENGTH: 17
<212> TYPE: DNA
<213> ORGANISM: Artificial Sequence
<220> FEATURE:
<223> OTHER INFORMATION: Synthetic oligomer

<400> SEQUENCE: 73
ttgaggggca tcgtcgc                                                 17

<210> SEQ ID NO 74
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 74
tgaggggcat cgtcgc                                                  16

<210> SEQ ID NO 75
<211> LENGTH: 15
<212> TYPE: DNA
<213> ORGANISM: Artificial Sequence
<220> FEATURE:
<223> OTHER INFORMATION: Synthetic oligomer

<400> SEQUENCE: 75
gaggggcatc gtcgc                                                   15

<210> SEQ ID NO 76
<211> LENGTH: 14
<212> TYPE: DNA
<213> ORGANISM: Artificial Sequence
<220> FEATURE:
<223> OTHER INFORMATION: Synthetic oligomer

<400> SEQUENCE: 76
aggggcatcg tcgc                                                    14

<210> SEQ ID NO 77
<211> LENGTH: 13
<212> TYPE: DNA
<213> ORGANISM: Artificial Sequence
<220> FEATURE:
<223> OTHER INFORMATION: Synthetic oligomer

<400> SEQUENCE: 77
```

```
ggggcatcgt cgc                                                          13
```

<210> SEQ ID NO 78
<211> LENGTH: 12
<212> TYPE: DNA
<213> ORGANISM: Artificial Sequence
<220> FEATURE:
<223> OTHER INFORMATION: Synthetic oligomer

<400> SEQUENCE: 78

```
gggcatcgtc gc                                                           12
```

<210> SEQ ID NO 79
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 79

```
ggcatcgtcg c                                                            11
```

<210> SEQ ID NO 80
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 80

```
gcatcgtcgc                                                              10
```

<210> SEQ ID NO 81
<211> LENGTH: 9
<212> TYPE: DNA
<213> ORGANISM: Artificial Sequence
<220> FEATURE:
<223> OTHER INFORMATION: Synthetic oligomer

<400> SEQUENCE: 81

```
catcgtcgc                                                                9
```

<210> SEQ ID NO 82
<211> LENGTH: 8
<212> TYPE: DNA
<213> ORGANISM: Artificial Sequence
<220> FEATURE:
<223> OTHER INFORMATION: Synthetic oligomer

<400> SEQUENCE: 82

```
atcgtcgc                                                                 8
```

<210> SEQ ID NO 83
<211> LENGTH: 7
<212> TYPE: DNA
<213> ORGANISM: Artificial Sequence
<220> FEATURE:
<223> OTHER INFORMATION: Synthetic oligomer

<400> SEQUENCE: 83

```
tcgtcgc                                                                  7
```

<210> SEQ ID NO 84
<211> LENGTH: 20
<212> TYPE: DNA
<213> ORGANISM: Artificial Sequence

```
<220> FEATURE:
<223> OTHER INFORMATION: Synthetic oligomer

<400> SEQUENCE: 84
ggaaaccgtt gtggtctccc                                              20

<210> SEQ ID NO 85
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 85
accgttgtgg tctccc                                                  16

<210> SEQ ID NO 86
<211> LENGTH: 13
<212> TYPE: DNA
<213> ORGANISM: Artificial Sequence
<220> FEATURE:
<223> OTHER INFORMATION: Synthetic oligomer

<400> SEQUENCE: 86
gttgtggtct ccc                                                     13

<210> SEQ ID NO 87
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 87
gtggtctccc                                                         10

<210> SEQ ID NO 88
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 88
cgtcgcggga ttccttct                                                18

<210> SEQ ID NO 89
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 89
aaagttaaac aaaattat                                                18

<210> SEQ ID NO 90
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 90
tccttcttaa agttaaac                                                18
```

<210> SEQ ID NO 91
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 91
cgttgagggg                                                              10

<210> SEQ ID NO 92
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 92
gttgaggggc                                                              10

<210> SEQ ID NO 93
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 93
ttgaggggca                                                              10

<210> SEQ ID NO 94
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 94
tgaggggcat                                                              10

<210> SEQ ID NO 95
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 95
gaggggcatc                                                              10

<210> SEQ ID NO 96
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 96
aggggcatcg                                                              10

<210> SEQ ID NO 97
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 97
ggggcatcgt                                                                            10

<210> SEQ ID NO 98
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 98
gggcatcgtc                                                                            10

<210> SEQ ID NO 99
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 99
ggcatcgtcg                                                                            10

<210> SEQ ID NO 100
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 100
aatagggttg g                                                                          11

<210> SEQ ID NO 101
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 101
tttgcaaccc c                                                                          11

<210> SEQ ID NO 102
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 102
atcctcccaa cttcgacata                                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 103
tgccgagcac cggcttcata                                                                 20

<210> SEQ ID NO 104

```
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 104
tccacttgcc                                                            10

<210> SEQ ID NO 105
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 105
ttcttcgata gtgctcatac                                                 20

<210> SEQ ID NO 106
<211> LENGTH: 18
<212> TYPE: DNA
<213> ORGANISM: Artificial Sequence
<220> FEATURE:
<223> OTHER INFORMATION: Synthetic oligomer

<400> SEQUENCE: 106
tcttcgatag tgctcata                                                   18

<210> SEQ ID NO 107
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 107
cttcgatagt gctcat                                                     16

<210> SEQ ID NO 108
<211> LENGTH: 14
<212> TYPE: DNA
<213> ORGANISM: Artificial Sequence
<220> FEATURE:
<223> OTHER INFORMATION: Synthetic oligomer

<400> SEQUENCE: 108
tcgatagtgc tcat                                                       14

<210> SEQ ID NO 109
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 109
cttcgatagt g                                                          11

<210> SEQ ID NO 110
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 110
```

```
ttcgatagtg                                                          10

<210> SEQ ID NO 111
<211> LENGTH: 9
<212> TYPE: DNA
<213> ORGANISM: Artificial Sequence
<220> FEATURE:
<223> OTHER INFORMATION: Synthetic oligomer

<400> SEQUENCE: 111 ttcgatagt                                                            9

<210> SEQ ID NO 112
<211> LENGTH: 8
<212> TYPE: DNA
<213> ORGANISM: Artificial Sequence
<220> FEATURE:
<223> OTHER INFORMATION: Synthetic oligomer

<400> SEQUENCE: 112 tcgatagt                                                             8

<210> SEQ ID NO 113
<211> LENGTH: 7
<212> TYPE: DNA
<213> ORGANISM: Artificial Sequence
<220> FEATURE:
<223> OTHER INFORMATION: Synthetic oligomer

<400> SEQUENCE: 113 tcgatag                                                              7

<210> SEQ ID NO 114
<211> LENGTH: 6
<212> TYPE: DNA
<213> ORGANISM: Artificial Sequence
<220> FEATURE:
<223> OTHER INFORMATION: Synthetic oligomer

<400> SEQUENCE: 114 cgatag                                                               6

<210> SEQ ID NO 115
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 115
ttgtcctgaa tatcacttcg                                               20

<210> SEQ ID NO 116
<211> LENGTH: 16
<212> TYPE: DNA
<213> ORGANISM: Artificial Sequence
<220> FEATURE:
<223> OTHER INFORMATION: Synthetic oligomer

<400> SEQUENCE: 116
gtcctgaata tcactt                                                   16

<210> SEQ ID NO 117
<211> LENGTH: 14
<212> TYPE: DNA
```

```
<213> ORGANISM: Artificial Sequence
<220> FEATURE:
<223> OTHER INFORMATION: Synthetic oligomer

<400> SEQUENCE: 117
tcgtgagtat cact                                                        14

<210> SEQ ID NO 118
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 118
tctcagatgg t                                                           11

<210> SEQ ID NO 119
<211> LENGTH: 7
<212> TYPE: DNA
<213> ORGANISM: Artificial Sequence
<220> FEATURE:
<223> OTHER INFORMATION: Synthetic oligomer

<400> SEQUENCE: 119 aatcgga                                                                 7

<210> SEQ ID NO 120
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 120
acgttgaggc                                                             10

<210> SEQ ID NO 121
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 121
tccacttgcc                                                             10

<210> SEQ ID NO 122
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 122
ttccattggt tcaaacatag                                                  20

<210> SEQ ID NO 123
<211> LENGTH: 10
<212> TYPE: DNA
<213> ORGANISM: Artificial Sequence
<220> FEATURE:
<223> OTHER INFORMATION: Synthetic oligomer

<400> SEQUENCE: 123
ccattggttc                                                             10
```

<210> SEQ ID NO 124
<211> LENGTH: 20
<212> TYPE: DNA
<213> ORGANISM: Artificial Sequence
<220> FEATURE:
<223> OTHER INFORMATION: Synthetic oligomer

<400> SEQUENCE: 124
ctctcgcaag gtcgctcatc                                           20

<210> SEQ ID NO 125
<211> LENGTH: 11
<212> TYPE: DNA
<213> ORGANISM: Artificial Sequence
<220> FEATURE:
<223> OTHER INFORMATION: Synthetic oligomer

<400> SEQUENCE: 125
ctctcgcaag g                                                    11

<210> SEQ ID NO 126
<211> LENGTH: 11
<212> TYPE: DNA
<213> ORGANISM: Escherichia coli

<400> SEQUENCE: 126
tgctcatact c                                                    11

<210> SEQ ID NO 127
<211> LENGTH: 11
<212> TYPE: DNA
<213> ORGANISM: Escherichia coli

<400> SEQUENCE: 127
atagtgctca t                                                    11

<210> SEQ ID NO 128
<211> LENGTH: 11
<212> TYPE: DNA
<213> ORGANISM: Escherichia coli

<400> SEQUENCE: 128
gcgttcttcc g                                                    11